US009814758B2

(12) United States Patent
Barrere et al.

(10) Patent No.: US 9,814,758 B2
(45) Date of Patent: Nov. 14, 2017

(54) INHIBITORS OF APOPTOSIS AND USES THEREOF

(75) Inventors: Stéphanie Barrere, Vendemian (FR);
Joël Nargeot, Montpellier (FR);
Bernard Lebleu, Montpellier (FR);
Prisca Boisguerin, Le Grand-du-Roi (FR); Christophe Piot, Saint Clement de Riviere (FR)

(73) Assignees: CENTRE NATIONAL DE LA RECHERCHE SCIENTIFIQUE-CNRS, Paris (FR);
UNIVERSITE MONTPELLIER 2-SCIENCES ET TECHNIQUE, Montpellier (FR); UNIVERSITE DE MONTPELLIER 1, Montpellier (FR)

( * ) Notice: Subject to any disclaimer, the term of this patent is extended or adjusted under 35 U.S.C. 154(b) by 2 days.

(21) Appl. No.: 13/885,956

(22) PCT Filed: Nov. 17, 2011

(86) PCT No.: PCT/EP2011/070404
§ 371 (c)(1),
(2), (4) Date: May 16, 2013

(87) PCT Pub. No.: WO2012/066103
PCT Pub. Date: May 24, 2012

(65) Prior Publication Data
US 2013/0288979 A1    Oct. 31, 2013

(30) Foreign Application Priority Data
Nov. 18, 2010   (WO) .................. PCT/IB2010/003158

(51) Int. Cl.
*A61K 45/06*    (2006.01)
*A61K 38/08*    (2006.01)
*A61K 38/17*    (2006.01)
*C07K 14/47*    (2006.01)
*A61K 38/10*    (2006.01)

(52) U.S. Cl.
CPC .......... *A61K 38/1709* (2013.01); *A61K 38/08* (2013.01); *A61K 38/10* (2013.01); *A61K 45/06* (2013.01); *C07K 14/4747* (2013.01)

(58) Field of Classification Search
None
See application file for complete search history.

(56) References Cited

FOREIGN PATENT DOCUMENTS

| KR | 2005 0107007 A | 11/2005 |
| WO | WO-98/34946 A1 | 8/1998 |
| WO | WO 9834946 A1 * | 8/1998 |
| WO | WO-2010/006177 A2 | 1/2010 |

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Carrington et al., The structure of FADD and its mode of interaction with procaspase-8, *Molecular Cell*, 22(5):599-610 (2006).
Chen et al., DAXX interacts with phage Phi C31 intergrase and inhibits recombination, *Nucl. Acids Res.*, 34(21):6298-304 (2006).
Genbank Accession No. A2V6V1, Full death-associated protein 6, Mar. 20, 2007.
Jung et al., Subcellular localization of DAXX determines its opposing functions in ischemic cell death, *FEBS Letters*, 581(5):843-52 (2007).
Lee et al., Death effector domain of a mammalian apoptosis mediator, FADD, induces bacterial cell death, *Molec. Microbiol.*, 35(6):1540-9 (2000).
Roubille et al., Myocardial expression of a dominant-negative form of DAXX decreases infarct size and attenuates apoptosis in an in vivo mouse model of ischemia/reperfusion injury, *Circulation*, 116:2709-17 (2007).
Sandu et al., FADD self-assocation is required for stable interaction with an activated death receptor, *Cell Death*, 13(12):2052-61 (2006).
Werner et al., Emerging roles for the death adaptor FADD in death receptor avidity and cell cycle regulation, *Cell Cycle*, 5(20):2332-8 (2006).
International Search Report of the International Searching Authority, European Patent Office , PCT/EP2011/070404, dated May 24, 2012.
International Search Report of the International Searching Authority, European Patent Office, PCT/IB2010/003158, dated Apr. 28, 2011.

* cited by examiner

*Primary Examiner* — Brian J Gangle
*Assistant Examiner* — Andrea McCollum
(74) *Attorney, Agent, or Firm* — Marshall, Gerstein & Borun LLP

(57) ABSTRACT

The invention relates to fragments of the Death-Domain Associated protein (DAXX protein) and of the Fas-Associated Death Domain protein (FADD protein) that inhibit cell apoptosis, in particular cell apoptosis mediated by the Fas receptor. The invention also relates to derivatives of said anti-apoptotic fragments, conjugates comprising said fragments, pharmaceutical compositions comprising said fragments, and to the medical applications of said fragments, derivatives, conjugates, and pharmaceutical compositions thereof in the treatment or prevention of diseases and conditions associated with apoptosis.

21 Claims, 18 Drawing Sheets

A ncDAXXp  AKLYVYINELCTVLK

|  |  |
|---|---|
| DAXXp-209 | SGPPCKKSRKEKKQT |
| DAXXp-210 | PCKKSRKEKKQTGSG |
| DAXXp-211 | KSRKEKKQTGSGPLG |
| DAXXp-212 | KEKKQTGSGPLGNSY |
| DAXXp | KKSRKEKKQTGSGPLG |

B

```
582 ISFFRKQSEEPFTTVLENGAGMVSSTSFNGGVSPHNWGDSGPPCKKSRKEKKQTGSGPLG 641 DAXX_CHLAE
586 ISSSRKQSEEPFTTVLENGAGMVSSTSFNGGVSPHNWGDSGPPCKKSRKEKKQTGSGPLG 645 DAXX_HUMAN
584 ISSSRKQSEEPLTTVLENGAAMVTSTSFNGGVSPHTWGDSCPPCKKSRKEK-ETGAEPLG 642 DAXX_CANFA
586 ISSPRKKSEDSLPTILENGAAVVTSTSVNGRVSSHTWRDASPPSKRFRKEKKQLGSGLLG 645 DAXX_MOUSE
577 ISSSRRKSDSSLPTILENGAAMVTSTSFNGRVSSHPCRDASPPSKRFRKEKKQLGPGPLG 636 DAXX_RAT
     **  *::*:..:.*:*****.:*:***.** **.*   *: **.*: ****  :  *.  **
```

Figure 1

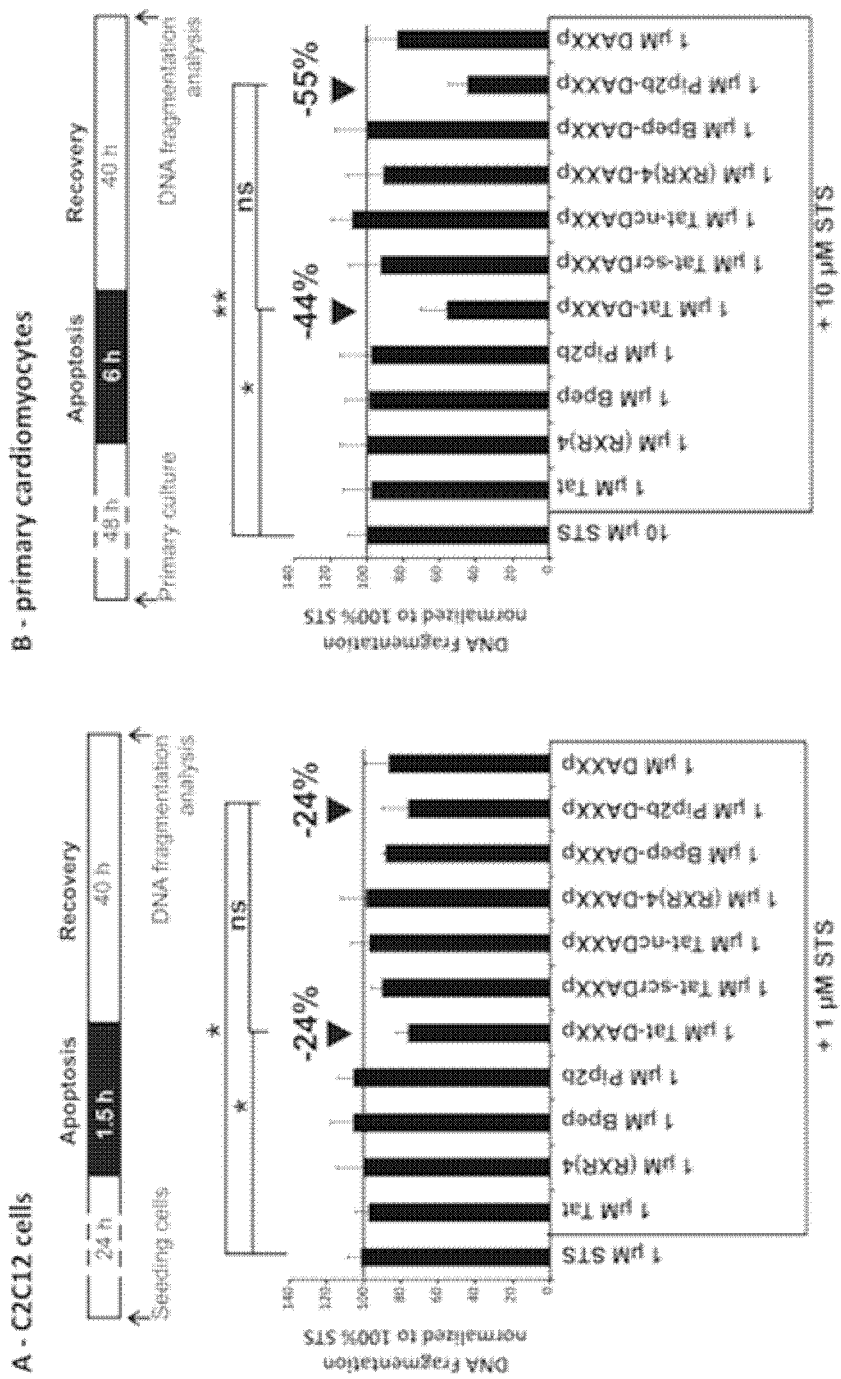
Figure 5(A) -(B)

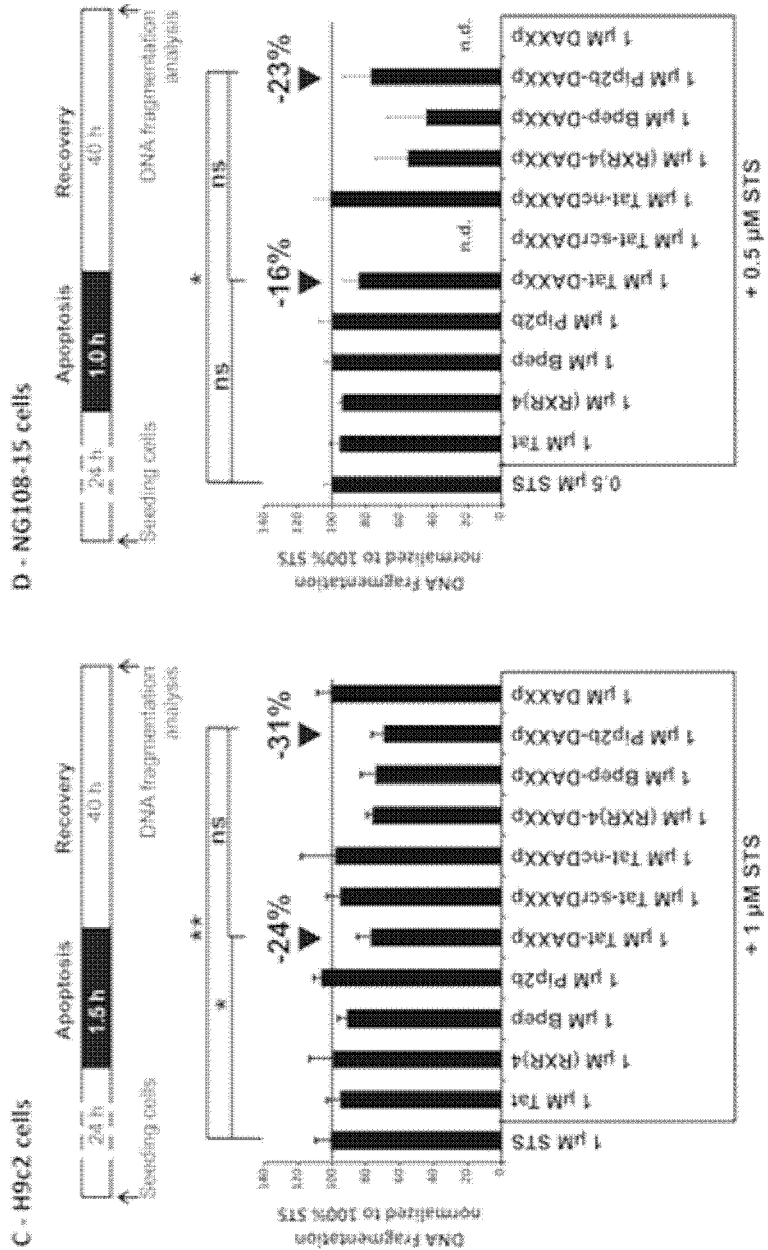
Figure 5(C) -(D)

A
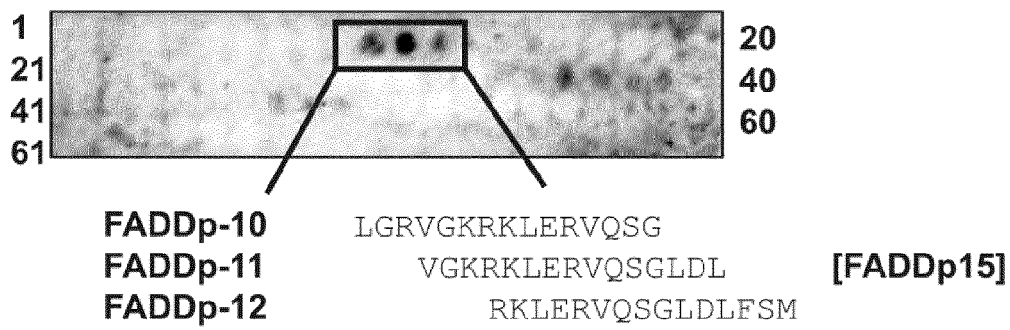
FADDp-10    LGRVGKRKLERVQSG
FADDp-11        VGKRKLERVQSGLDL      [FADDp15]
FADDp-12            RKLERVQSGLDLFSM
B
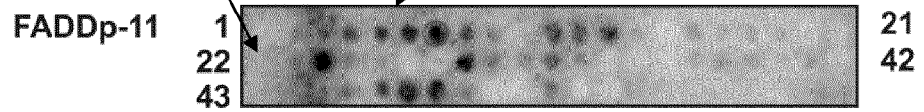
FADDp-11 (spot no. 6)     KRKLERVQSGLDL
FADDp-11 (spot no. 24)    KRKLERVQS            [FADDp]
Figure 8

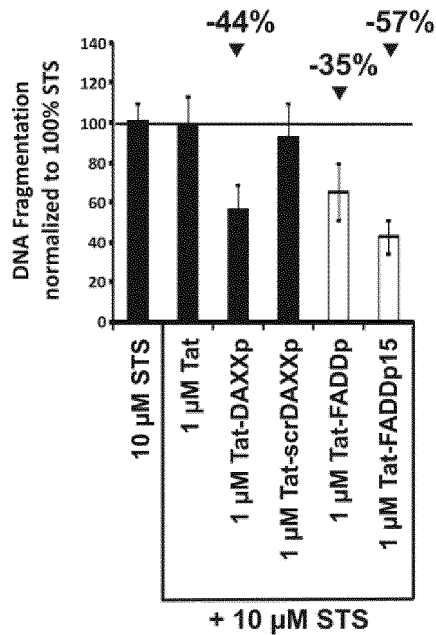
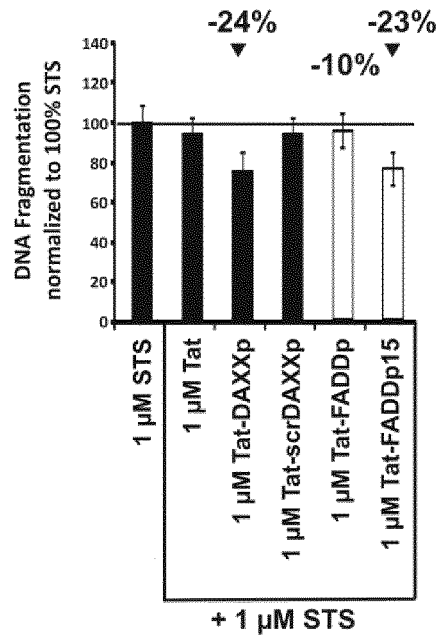
Figure 9

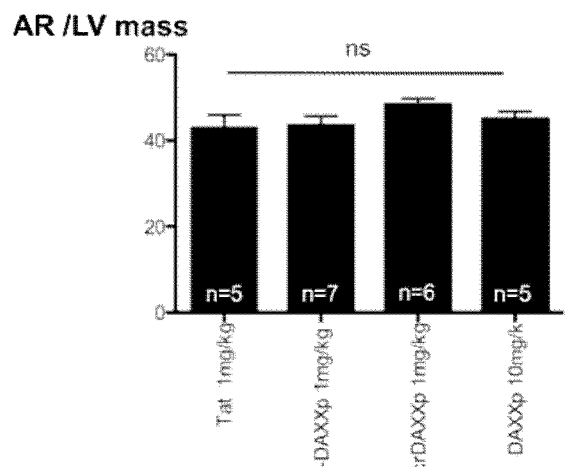
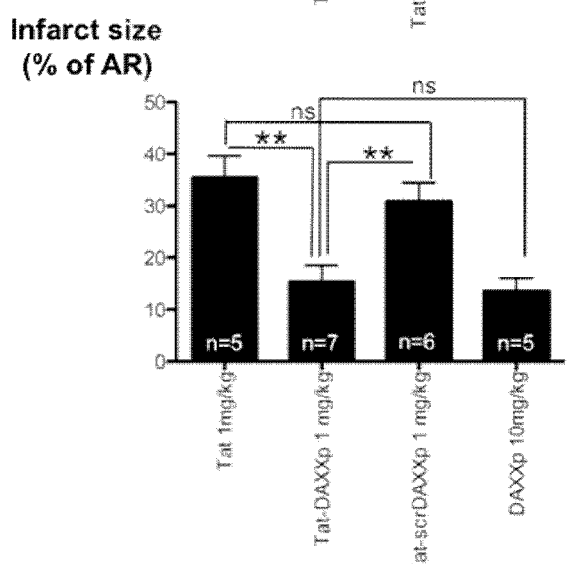
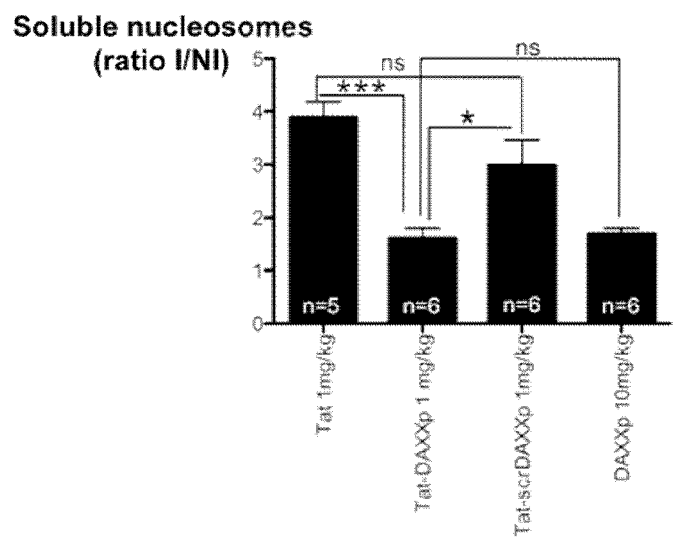
Figure 12

A  AR /LV mass
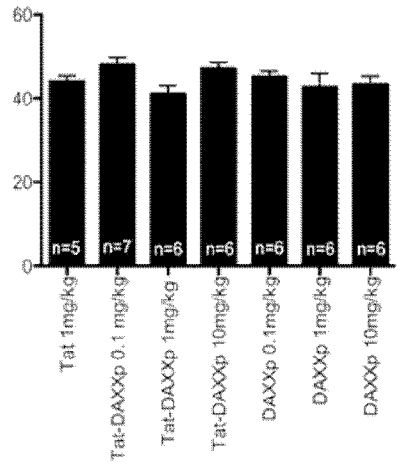
B
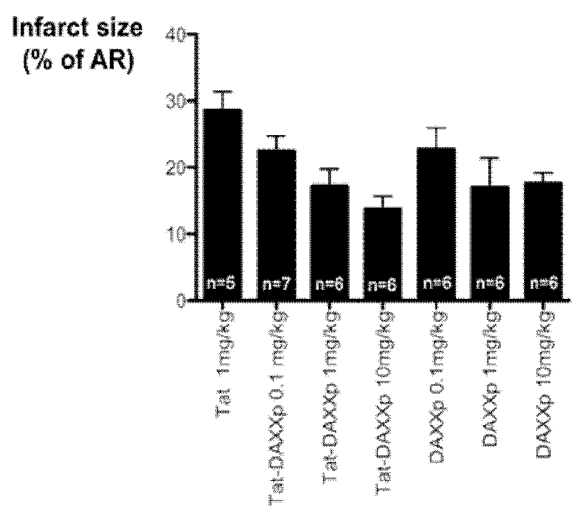
C
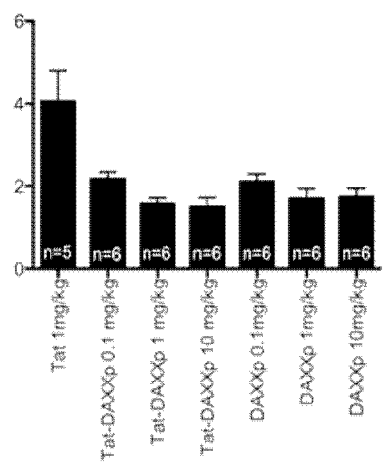
Figure 15

SEQUENCE LISTING

<160> NUMBER OF SEQ ID NOS: 76

<210> SEQ ID NO 1
<211> LENGTH: 740
<212> TYPE: PRT
<213> ORGANISM: Homo sapiens

<400> SEQUENCE: 1

Met Ala Thr Ala Asn Ser Ile Ile Val Leu Asp Asp Asp Glu Asp
1               5                   10                  15

Glu Ala Ala Ala Gln Pro Gly Pro Ser His Pro Leu Pro Asn Ala Ala
                20                  25                  30

Ser Pro Gly Ala Glu Ala Pro Ser Ser Ser Glu Pro His Gly Ala Arg
            35                  40                  45

Gly Ser Ser Ser Ser Gly Gly Lys Lys Cys Tyr Lys Leu Glu Asn Glu
    50                  55                  60

Lys Leu Phe Glu Glu Phe Leu Glu Leu Cys Lys Met Gln Thr Ala Asp
65                  70                  75                  80

His Pro Glu Val Val Pro Phe Leu Tyr Asn Arg Gln Gln Arg Ala His
                85                  90                  95

Ser Leu Phe Leu Ala Ser Ala Glu Phe Cys Asn Ile Leu Ser Arg Val
                100                 105                 110

Leu Ser Arg Ala Arg Ser Arg Pro Ala Lys Leu Tyr Val Tyr Ile Asn
            115                 120                 125

Glu Leu Cys Thr Val Leu Lys Ala His Ser Ala Lys Lys Lys Leu Asn
    130                 135                 140

Leu Ala Pro Ala Ala Thr Thr Ser Asn Glu Pro Ser Gly Asn Asn Pro
145                 150                 155                 160

Pro Thr His Leu Ser Leu Asp Pro Thr Asn Ala Glu Asn Thr Ala Ser
                165                 170                 175

Gln Ser Pro Arg Thr Arg Gly Ser Arg Arg Gln Ile Gln Arg Leu Glu
                180                 185                 190

Gln Leu Leu Ala Leu Tyr Val Ala Glu Ile Arg Arg Leu Gln Glu Lys
            195                 200                 205

Glu Leu Asp Leu Ser Glu Leu Asp Asp Pro Asp Ser Ala Tyr Leu Gln
    210                 215                 220

-continued

Glu Ala Arg Leu Lys Arg Lys Leu Ile Arg Leu Phe Gly Arg Leu Cys
225                 230                 235                 240

Glu Leu Lys Asp Cys Ser Ser Leu Thr Gly Arg Val Ile Glu Gln Arg
            245                 250                 255

Ile Pro Tyr Arg Gly Thr Arg Tyr Pro Glu Val Asn Arg Arg Ile Glu
        260                 265                 270

Arg Leu Ile Asn Lys Pro Gly Pro Asp Thr Phe Pro Asp Tyr Gly Asp
    275                 280                 285

Val Leu Arg Ala Val Glu Lys Ala Ala Arg His Ser Leu Gly Leu
290                 295                 300

Pro Arg Gln Gln Leu Gln Leu Met Ala Gln Asp Ala Phe Arg Asp Val
305                 310                 315                 320

Gly Ile Arg Leu Gln Glu Arg Arg His Leu Asp Leu Ile Tyr Asn Phe
                325                 330                 335

Gly Cys His Leu Thr Asp Asp Tyr Arg Pro Gly Val Asp Pro Ala Leu
            340                 345                 350

Ser Asp Pro Val Leu Ala Arg Arg Leu Arg Glu Asn Arg Ser Leu Ala
        355                 360                 365

Met Ser Arg Leu Asp Glu Val Ile Ser Lys Tyr Ala Met Leu Gln Asp
370                 375                 380

Lys Ser Glu Glu Gly Glu Arg Lys Lys Arg Arg Ala Arg Leu Gln Gly
385                 390                 395                 400

Thr Ser Ser His Ser Ala Asp Thr Pro Glu Ala Ser Leu Asp Ser Gly
                405                 410                 415

Glu Gly Pro Ser Gly Met Ala Ser Gln Gly Cys Pro Ser Ala Ser Arg
            420                 425                 430

Ala Glu Thr Asp Asp Glu Asp Asp Glu Glu Ser Asp Glu Glu Glu
            435                 440                 445

Glu Glu Glu Glu Glu Glu Glu Glu Ala Thr Asp Ser Glu Glu Glu
450                 455                 460

Glu Asp Leu Glu Gln Met Gln Glu Gly Gln Asp Asp Glu Glu Glu
465                 470                 475                 480

Asp Glu Glu Glu Glu Ala Ala Ala Gly Lys Asp Gly Asp Lys Ser Pro
                485                 490                 495

Met Ser Ser Leu Gln Ile Ser Asn Glu Lys Asn Leu Glu Pro Gly Lys
            500                 505                 510

Gln Ile Ser Arg Ser Ser Gly Glu Gln Gln Asn Lys Gly Arg Ile Val
        515                 520                 525

Ser Pro Ser Leu Leu Ser Glu Glu Pro Leu Ala Pro Ser Ser Ile Asp
    530                 535                 540

Ala Glu Ser Asn Gly Glu Gln Pro Glu Glu Leu Thr Leu Glu Glu Glu
545                 550                 555                 560

Ser Pro Val Ser Gln Leu Phe Glu Leu Glu Ile Glu Ala Leu Pro Leu
                565                 570                 575

Asp Thr Pro Ser Ser Val Glu Asp Ile Ser Ser Ser Arg Lys Gln
            580                 585                 590

Ser Glu Glu Pro Phe Thr Thr Val Leu Glu Asn Gly Ala Gly Met Val
        595                 600                 605

Ser Ser Thr Ser Phe Asn Gly Gly Val Ser Pro His Asn Trp Gly Asp
    610                 615                 620

Ser Gly Pro Pro Cys Lys Lys Ser Arg Lys Glu Lys Lys Gln Thr Gly
625                 630                 635                 640

Ser Gly Pro Leu Gly Asn Ser Tyr Val Glu Arg Gln Arg Ser Val His

```
            645                 650                 655
Glu Lys Asn Gly Lys Lys Ile Cys Thr Leu Pro Ser Pro Pro Ser Pro
            660                 665                 670

Leu Ala Ser Leu Ala Pro Val Ala Asp Ser Ser Thr Arg Val Asp Ser
        675                 680                 685

Pro Ser His Gly Leu Val Thr Ser Ser Leu Cys Ile Pro Ser Pro Ala
    690                 695                 700

Arg Leu Ser Gln Thr Pro His Ser Gln Pro Pro Arg Pro Gly Thr Cys
705                 710                 715                 720

Lys Thr Ser Val Ala Thr Gln Cys Asp Pro Glu Glu Ile Ile Val Leu
                725                 730                 735

Ser Asp Ser Asp
            740

<210> SEQ ID NO 2
<211> LENGTH: 15
<212> TYPE: PRT
<213> ORGANISM: Homo sapiens

<400> SEQUENCE: 2

Lys Ser Arg Lys Glu Lys Lys Gln Thr Gly Ser Gly Pro Leu Gly
1               5                   10                  15

<210> SEQ ID NO 3
<211> LENGTH: 15
<212> TYPE: PRT
<213> ORGANISM: Homo sapiens

<400> SEQUENCE: 3

Ser Gly Pro Pro Cys Lys Lys Ser Arg Lys Glu Lys Lys Gln Thr
1               5                   10                  15

<210> SEQ ID NO 4
<211> LENGTH: 15
<212> TYPE: PRT
<213> ORGANISM: Homo sapiens

<400> SEQUENCE: 4

Pro Cys Lys Lys Ser Arg Lys Glu Lys Lys Gln Thr Gly Ser Gly
1               5                   10                  15

<210> SEQ ID NO 5
<211> LENGTH: 16
<212> TYPE: PRT
<213> ORGANISM: Homo sapiens

<400> SEQUENCE: 5

Lys Lys Ser Arg Lys Glu Lys Lys Gln Thr Gly Ser Gly Pro Leu Gly
1               5                   10                  15

<210> SEQ ID NO 6
<211> LENGTH: 14
<212> TYPE: PRT
<213> ORGANISM: Homo sapiens

<400> SEQUENCE: 6

Ser Arg Lys Glu Lys Lys Gln Thr Gly Ser Gly Pro Leu Gly
1               5                   10

<210> SEQ ID NO 7
<211> LENGTH: 15
<212> TYPE: PRT
```

```
<213> ORGANISM: Homo sapiens

<400> SEQUENCE: 7

Lys Glu Lys Lys Gln Thr Gly Ser Gly Pro Leu Gly Asn Ser Tyr
1               5                   10                  15

<210> SEQ ID NO 8
<211> LENGTH: 208
<212> TYPE: PRT
<213> ORGANISM: Homo sapiens

<400> SEQUENCE: 8

Met Asp Pro Phe Leu Val Leu Leu His Ser Val Ser Ser Leu Ser
1               5                   10                  15

Ser Ser Glu Leu Thr Glu Leu Lys Phe Leu Cys Leu Gly Arg Val Gly
                20                  25                  30

Lys Arg Lys Leu Glu Arg Val Gln Ser Gly Leu Asp Leu Phe Ser Met
                35                  40                  45

Leu Leu Glu Gln Asn Asp Leu Glu Pro Gly His Thr Glu Leu Leu Arg
        50                  55                  60

Glu Leu Leu Ala Ser Leu Arg Arg His Asp Leu Leu Arg Arg Val Asp
65                  70                  75                  80

Asp Phe Glu Ala Gly Ala Ala Gly Ala Ala Pro Gly Glu Glu Asp
                85                  90                  95

Leu Cys Ala Ala Phe Asn Val Ile Cys Asp Asn Val Gly Lys Asp Trp
                100                 105                 110

Arg Arg Leu Ala Arg Gln Leu Lys Val Ser Asp Thr Lys Ile Asp Ser
                115                 120                 125

Ile Glu Asp Arg Tyr Pro Arg Asn Leu Thr Glu Arg Val Arg Glu Ser
        130                 135                 140

Leu Arg Ile Trp Lys Asn Thr Glu Lys Glu Asn Ala Thr Val Ala His
145                 150                 155                 160

Leu Val Gly Ala Leu Arg Ser Cys Gln Met Asn Leu Val Ala Asp Leu
                165                 170                 175

Val Gln Glu Val Gln Gln Ala Arg Asp Leu Gln Asn Arg Ser Gly Ala
                180                 185                 190

Met Ser Pro Met Ser Trp Asn Ser Asp Ala Ser Thr Ser Glu Ala Ser
        195                 200                 205

<210> SEQ ID NO 9
<211> LENGTH: 15
<212> TYPE: PRT
<213> ORGANISM: Homo sapiens

<400> SEQUENCE: 9

Val Gly Lys Arg Lys Leu Glu Arg Val Gln Ser Gly Leu Asp Leu
1               5                   10                  15

<210> SEQ ID NO 10
<211> LENGTH: 15
<212> TYPE: PRT
<213> ORGANISM: Homo sapiens

<400> SEQUENCE: 10

Leu Gly Arg Val Gly Lys Arg Lys Leu Glu Arg Val Gln Ser Gly
1               5                   10                  15

<210> SEQ ID NO 11
<211> LENGTH: 15
```

```
<212> TYPE: PRT
<213> ORGANISM: Homo sapiens

<400> SEQUENCE: 11

Arg Lys Leu Glu Arg Val Gln Ser Gly Leu Asp Leu Phe Ser Met
1               5                   10                  15

<210> SEQ ID NO 12
<211> LENGTH: 9
<212> TYPE: PRT
<213> ORGANISM: Homo sapiens

<400> SEQUENCE: 12

Lys Arg Lys Leu Glu Arg Val Gln Ser
1               5

<210> SEQ ID NO 13
<211> LENGTH: 15
<212> TYPE: PRT
<213> ORGANISM: Homo sapiens

<400> SEQUENCE: 13

Ala Lys Leu Tyr Val Tyr Ile Asn Glu Leu Cys Thr Val Leu Lys
1               5                   10                  15

<210> SEQ ID NO 14
<211> LENGTH: 13
<212> TYPE: PRT
<213> ORGANISM: Homo sapiens

<400> SEQUENCE: 14

Arg Lys Glu Lys Lys Gln Thr Gly Ser Gly Pro Leu Gly
1               5                   10

<210> SEQ ID NO 15
<211> LENGTH: 16
<212> TYPE: PRT
<213> ORGANISM: Mus musculus

<400> SEQUENCE: 15

Lys Arg Phe Arg Lys Glu Lys Lys Gln Leu Gly Ser Gly Leu Leu Gly
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: scrambled sequence

<400> SEQUENCE: 16

Lys Lys Gly Arg Lys Gln Ser Gly Glu Ser Leu Gly Thr Pro Lys Lys
1               5                   10                  15

<210> SEQ ID NO 17
<211> LENGTH: 17
<212> TYPE: PRT
<213> ORGANISM: Homo sapiens

<400> SEQUENCE: 17

Lys Lys Ser Arg Lys Glu Lys Lys Gln Thr Gly Ser Gly Pro Leu Gly
1               5                   10                  15
Asn
```

```
<210> SEQ ID NO 18
<211> LENGTH: 18
<212> TYPE: PRT
<213> ORGANISM: Homo sapiens

<400> SEQUENCE: 18

Lys Lys Ser Arg Lys Glu Lys Lys Gln Thr Gly Ser Gly Pro Leu Gly
1               5                   10                  15

Asn Ser

<210> SEQ ID NO 19
<211> LENGTH: 19
<212> TYPE: PRT
<213> ORGANISM: Homo sapiens

<400> SEQUENCE: 19

Lys Lys Ser Arg Lys Glu Lys Lys Gln Thr Gly Ser Gly Pro Leu Gly
1               5                   10                  15

Asn Ser Tyr

<210> SEQ ID NO 20
<211> LENGTH: 20
<212> TYPE: PRT
<213> ORGANISM: Homo sapiens

<400> SEQUENCE: 20

Lys Lys Ser Arg Lys Glu Lys Lys Gln Thr Gly Ser Gly Pro Leu Gly
1               5                   10                  15

Asn Ser Tyr Val
            20

<210> SEQ ID NO 21
<211> LENGTH: 17
<212> TYPE: PRT
<213> ORGANISM: Homo sapiens

<400> SEQUENCE: 21

Cys Lys Lys Ser Arg Lys Glu Lys Lys Gln Thr Gly Ser Gly Pro Leu
1               5                   10                  15

Gly

<210> SEQ ID NO 22
<211> LENGTH: 18
<212> TYPE: PRT
<213> ORGANISM: Homo sapiens

<400> SEQUENCE: 22

Pro Cys Lys Lys Ser Arg Lys Glu Lys Lys Gln Thr Gly Ser Gly Pro
1               5                   10                  15

Leu Gly

<210> SEQ ID NO 23
<211> LENGTH: 19
<212> TYPE: PRT
<213> ORGANISM: Homo sapiens

<400> SEQUENCE: 23

Pro Pro Cys Lys Lys Ser Arg Lys Glu Lys Lys Gln Thr Gly Ser Gly
1               5                   10                  15

Pro Leu Gly
```

-continued

```
<210> SEQ ID NO 24
<211> LENGTH: 20
<212> TYPE: PRT
<213> ORGANISM: Homo sapiens

<400> SEQUENCE: 24

Gly Pro Pro Cys Lys Lys Ser Arg Lys Glu Lys Lys Gln Thr Gly Ser
1               5                   10                  15

Gly Pro Leu Gly
            20

<210> SEQ ID NO 25
<211> LENGTH: 21
<212> TYPE: PRT
<213> ORGANISM: Homo sapiens

<400> SEQUENCE: 25

Ser Gly Pro Pro Cys Lys Lys Ser Arg Lys Glu Lys Lys Gln Thr Gly
1               5                   10                  15

Ser Gly Pro Leu Gly
            20

<210> SEQ ID NO 26
<211> LENGTH: 18
<212> TYPE: PRT
<213> ORGANISM: Homo sapiens

<400> SEQUENCE: 26

Cys Lys Lys Ser Arg Lys Glu Lys Lys Gln Thr Gly Ser Gly Pro Leu
1               5                   10                  15

Gly Asn

<210> SEQ ID NO 27
<211> LENGTH: 19
<212> TYPE: PRT
<213> ORGANISM: Homo sapiens

<400> SEQUENCE: 27

Cys Lys Lys Ser Arg Lys Glu Lys Lys Gln Thr Gly Ser Gly Pro Leu
1               5                   10                  15

Gly Asn Ser

<210> SEQ ID NO 28
<211> LENGTH: 20
<212> TYPE: PRT
<213> ORGANISM: Homo sapiens

<400> SEQUENCE: 28

Cys Lys Lys Ser Arg Lys Glu Lys Lys Gln Thr Gly Ser Gly Pro Leu
1               5                   10                  15

Gly Asn Ser Tyr
            20

<210> SEQ ID NO 29
<211> LENGTH: 21
<212> TYPE: PRT
<213> ORGANISM: Homo sapiens

<400> SEQUENCE: 29

Cys Lys Lys Ser Arg Lys Glu Lys Lys Gln Thr Gly Ser Gly Pro Leu
1               5                   10                  15

Gly Asn Ser Tyr Val
```

<210> SEQ ID NO 30
<211> LENGTH: 19
<212> TYPE: PRT
<213> ORGANISM: Homo sapiens

<400> SEQUENCE: 30

Pro Cys Lys Lys Ser Arg Lys Glu Lys Lys Gln Thr Gly Ser Gly Pro
1               5                   10                  15

Leu Gly Asn

<210> SEQ ID NO 31
<211> LENGTH: 20
<212> TYPE: PRT
<213> ORGANISM: Homo sapiens

<400> SEQUENCE: 31

Pro Cys Lys Lys Ser Arg Lys Glu Lys Lys Gln Thr Gly Ser Gly Pro
1               5                   10                  15

Leu Gly Asn Ser
            20

<210> SEQ ID NO 32
<211> LENGTH: 21
<212> TYPE: PRT
<213> ORGANISM: Homo sapiens

<400> SEQUENCE: 32

Pro Cys Lys Lys Ser Arg Lys Glu Lys Lys Gln Thr Gly Ser Gly Pro
1               5                   10                  15

Leu Gly Asn Ser Tyr
            20

<210> SEQ ID NO 33
<211> LENGTH: 22
<212> TYPE: PRT
<213> ORGANISM: Homo sapiens

<400> SEQUENCE: 33

Pro Cys Lys Lys Ser Arg Lys Glu Lys Lys Gln Thr Gly Ser Gly Pro
1               5                   10                  15

Leu Gly Asn Ser Tyr Val
            20

<210> SEQ ID NO 34
<211> LENGTH: 20
<212> TYPE: PRT
<213> ORGANISM: Homo sapiens

<400> SEQUENCE: 34

Pro Pro Cys Lys Lys Ser Arg Lys Glu Lys Lys Gln Thr Gly Ser Gly
1               5                   10                  15

Pro Leu Gly Asn
            20

<210> SEQ ID NO 35
<211> LENGTH: 21
<212> TYPE: PRT
<213> ORGANISM: Homo sapiens

<400> SEQUENCE: 35

Pro Pro Cys Lys Lys Ser Arg Lys Glu Lys Lys Gln Thr Gly Ser Gly
1               5                   10                  15

Pro Leu Gly Asn Ser
            20

<210> SEQ ID NO 36
<211> LENGTH: 22
<212> TYPE: PRT
<213> ORGANISM: Homo sapiens

<400> SEQUENCE: 36

Pro Pro Cys Lys Lys Ser Arg Lys Glu Lys Lys Gln Thr Gly Ser Gly
1               5                   10                  15

Pro Leu Gly Asn Ser Tyr
            20

<210> SEQ ID NO 37
<211> LENGTH: 23
<212> TYPE: PRT
<213> ORGANISM: Homo sapiens

<400> SEQUENCE: 37

Pro Pro Cys Lys Lys Ser Arg Lys Glu Lys Lys Gln Thr Gly Ser Gly
1               5                   10                  15

Pro Leu Gly Asn Ser Tyr Val
            20

<210> SEQ ID NO 38
<211> LENGTH: 21
<212> TYPE: PRT
<213> ORGANISM: Homo sapiens

<400> SEQUENCE: 38

Gly Pro Pro Cys Lys Lys Ser Arg Lys Glu Lys Lys Gln Thr Gly Ser
1               5                   10                  15

Gly Pro Leu Gly Asn
            20

<210> SEQ ID NO 39
<211> LENGTH: 22
<212> TYPE: PRT
<213> ORGANISM: Homo sapiens

<400> SEQUENCE: 39

Gly Pro Pro Cys Lys Lys Ser Arg Lys Glu Lys Lys Gln Thr Gly Ser
1               5                   10                  15

Gly Pro Leu Gly Asn Ser
            20

<210> SEQ ID NO 40
<211> LENGTH: 23
<212> TYPE: PRT
<213> ORGANISM: Homo sapiens

<400> SEQUENCE: 40

Gly Pro Pro Cys Lys Lys Ser Arg Lys Glu Lys Lys Gln Thr Gly Ser
1               5                   10                  15

Gly Pro Leu Gly Asn Ser Tyr
            20

<210> SEQ ID NO 41
<211> LENGTH: 24

-continued

```
<212> TYPE: PRT
<213> ORGANISM: Homo sapiens

<400> SEQUENCE: 41

Gly Pro Pro Cys Lys Lys Ser Arg Lys Glu Lys Lys Gln Thr Gly Ser
1               5                   10                  15
Gly Pro Leu Gly Asn Ser Tyr Val
            20

<210> SEQ ID NO 42
<211> LENGTH: 22
<212> TYPE: PRT
<213> ORGANISM: Homo sapiens

<400> SEQUENCE: 42

Ser Gly Pro Pro Cys Lys Lys Ser Arg Lys Glu Lys Lys Gln Thr Gly
1               5                   10                  15
Ser Gly Pro Leu Gly Asn
            20

<210> SEQ ID NO 43
<211> LENGTH: 23
<212> TYPE: PRT
<213> ORGANISM: Homo sapiens

<400> SEQUENCE: 43

Ser Gly Pro Pro Cys Lys Lys Ser Arg Lys Glu Lys Lys Gln Thr Gly
1               5                   10                  15
Ser Gly Pro Leu Gly Asn Ser
            20

<210> SEQ ID NO 44
<211> LENGTH: 24
<212> TYPE: PRT
<213> ORGANISM: Homo sapiens

<400> SEQUENCE: 44

Ser Gly Pro Pro Cys Lys Lys Ser Arg Lys Glu Lys Lys Gln Thr Gly
1               5                   10                  15
Ser Gly Pro Leu Gly Asn Ser Tyr
            20

<210> SEQ ID NO 45
<211> LENGTH: 10
<212> TYPE: PRT
<213> ORGANISM: Homo sapiens

<400> SEQUENCE: 45

Lys Arg Lys Leu Glu Arg Val Gln Ser Gly
1               5                   10

<210> SEQ ID NO 46
<211> LENGTH: 11
<212> TYPE: PRT
<213> ORGANISM: Homo sapiens

<400> SEQUENCE: 46

Lys Arg Lys Leu Glu Arg Val Gln Ser Gly Leu
1               5                   10

<210> SEQ ID NO 47
<211> LENGTH: 12
<212> TYPE: PRT
```

<213> ORGANISM: Homo sapiens

<400> SEQUENCE: 47

Lys Arg Lys Leu Glu Arg Val Gln Ser Gly Leu Asp
1               5                   10

<210> SEQ ID NO 48
<211> LENGTH: 13
<212> TYPE: PRT
<213> ORGANISM: Homo sapiens

<400> SEQUENCE: 48

Lys Arg Lys Leu Glu Arg Val Gln Ser Gly Leu Asp Leu
1               5                   10

<210> SEQ ID NO 49
<211> LENGTH: 10
<212> TYPE: PRT
<213> ORGANISM: Homo sapiens

<400> SEQUENCE: 49

Arg Lys Arg Lys Leu Glu Arg Val Gln Ser
1               5                   10

<210> SEQ ID NO 50
<211> LENGTH: 11
<212> TYPE: PRT
<213> ORGANISM: Homo sapiens

<400> SEQUENCE: 50

Lys Arg Lys Arg Lys Leu Glu Arg Val Gln Ser
1               5                   10

<210> SEQ ID NO 51
<211> LENGTH: 11
<212> TYPE: PRT
<213> ORGANISM: Homo sapiens

<400> SEQUENCE: 51

Gly Lys Arg Lys Leu Glu Arg Val Gln Ser Gly
1               5                   10

<210> SEQ ID NO 52
<211> LENGTH: 12
<212> TYPE: PRT
<213> ORGANISM: Homo sapiens

<400> SEQUENCE: 52

Gly Lys Arg Lys Leu Glu Arg Val Gln Ser Gly Leu
1               5                   10

<210> SEQ ID NO 53
<211> LENGTH: 13
<212> TYPE: PRT
<213> ORGANISM: Homo sapiens

<400> SEQUENCE: 53

Gly Lys Arg Lys Leu Glu Arg Val Gln Ser Gly Leu Asp
1               5                   10

<210> SEQ ID NO 54
<211> LENGTH: 14
<212> TYPE: PRT
<213> ORGANISM: Homo sapiens -continued

<400> SEQUENCE: 54

Gly Lys Arg Lys Leu Glu Arg Val Gln Ser Gly Leu Asp Leu
1               5                   10

<210> SEQ ID NO 55
<211> LENGTH: 12
<212> TYPE: PRT
<213> ORGANISM: Homo sapiens

<400> SEQUENCE: 55

Val Gly Lys Arg Lys Leu Glu Arg Val Gln Ser Gly
1               5                   10

<210> SEQ ID NO 56
<211> LENGTH: 13
<212> TYPE: PRT
<213> ORGANISM: Homo sapiens

<400> SEQUENCE: 56

Val Gly Lys Arg Lys Leu Glu Arg Val Gln Ser Gly Leu
1               5                   10

<210> SEQ ID NO 57
<211> LENGTH: 14
<212> TYPE: PRT
<213> ORGANISM: Homo sapiens

<400> SEQUENCE: 57

Val Gly Lys Arg Lys Leu Glu Arg Val Gln Ser Gly Leu Asp
1               5                   10

<210> SEQ ID NO 58
<211> LENGTH: 29
<212> TYPE: PRT
<213> ORGANISM: Artificial Sequence
<220> FEATURE:
<223> OTHER INFORMATION: conjugate Tat-DAXXp

<400> SEQUENCE: 58

Gly Arg Lys Lys Arg Arg Gln Arg Arg Arg Pro Pro Gln Lys Lys Ser
1               5                   10                  15

Arg Lys Glu Lys Lys Gln Thr Gly Ser Gly Pro Leu Gly
            20                  25

<210> SEQ ID NO 59
<211> LENGTH: 22
<212> TYPE: PRT
<213> ORGANISM: Artificial Sequence
<220> FEATURE:
<223> OTHER INFORMATION: conjugate Tat-FADDp

<400> SEQUENCE: 59

Gly Arg Lys Lys Arg Arg Gln Arg Arg Arg Pro Pro Gln Lys Arg Lys
1               5                   10                  15

Leu Glu Arg Val Gln Ser
            20

<210> SEQ ID NO 60
<211> LENGTH: 28
<212> TYPE: PRT
<213> ORGANISM: Artificial Sequence
<220> FEATURE:
<223> OTHER INFORMATION: conjugate Tat-FADDp15

<400> SEQUENCE: 60

```
Gly Arg Lys Lys Arg Arg Gln Arg Arg Pro Pro Gln Val Gly Lys
1               5                   10                  15

Arg Lys Leu Glu Arg Val Gln Ser Gly Leu Asp Leu
            20                  25

<210> SEQ ID NO 61
<211> LENGTH: 29
<212> TYPE: PRT
<213> ORGANISM: Artificial Sequence
<220> FEATURE:
<223> OTHER INFORMATION: conjugate Tat-mDAXXp

<400> SEQUENCE: 61

Gly Arg Lys Lys Arg Arg Gln Arg Arg Pro Pro Gln Lys Arg Phe
1               5                   10                  15

Arg Lys Glu Lys Lys Gln Leu Gly Ser Gly Leu Leu Gly
            20                  25

<210> SEQ ID NO 62
<211> LENGTH: 13
<212> TYPE: PRT
<213> ORGANISM: Artificial Sequence
<220> FEATURE:
<223> OTHER INFORMATION: Synthetic peptide

<400> SEQUENCE: 62

Gly Arg Lys Lys Arg Arg Gln Arg Arg Pro Pro Gln
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is amino-hexanoic acid
<220> FEATURE:
<221> NAME/KEY: MISC_FEATURE
<222> LOCATION: (5)..(5)
<223> OTHER INFORMATION: Xaa is amino-hexanoic acid
<220> FEATURE:
<221> NAME/KEY: MISC_FEATURE
<222> LOCATION: (8)..(8)
<223> OTHER INFORMATION: Xaa is amino-hexanoic acid
<220> FEATURE:
<221> NAME/KEY: MISC_FEATURE
<222> LOCATION: (11)..(11)
<223> OTHER INFORMATION: Xaa is amino-hexanoic acid

<400> SEQUENCE: 63

Arg Xaa Arg Arg Xaa Arg Arg Xaa Arg Arg Xaa Arg
1               5                   10

<210> SEQ ID NO 64
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is amino-hexanoic acid
<220> FEATURE:
<221> NAME/KEY: MISC_FEATURE
<222> LOCATION: (5)..(5)
```

```
<223> OTHER INFORMATION: Xaa is beta-Ala
<220> FEATURE:
<221> NAME/KEY: MISC_FEATURE
<222> LOCATION: (8)..(8)
<223> OTHER INFORMATION: Xaa is amino-hexanoic acid
<220> FEATURE:
<221> NAME/KEY: MISC_FEATURE
<222> LOCATION: (11)..(11)
<223> OTHER INFORMATION: Xaa is beta-Ala
<220> FEATURE:
<221> NAME/KEY: MISC_FEATURE
<222> LOCATION: (13)..(13)
<223> OTHER INFORMATION: Xaa is amino-hexanoic acid
<220> FEATURE:
<221> NAME/KEY: MISC_FEATURE
<222> LOCATION: (14)..(14)
<223> OTHER INFORMATION: Xaa is beta-Ala

<400> SEQUENCE: 64

Arg Xaa Arg Arg Xaa Arg Arg Xaa Arg Arg Xaa Arg Xaa Xaa
1               5                   10

<210> SEQ ID NO 65
<211> LENGTH: 23
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is amino-hexanoic acid
<220> FEATURE:
<221> NAME/KEY: MISC_FEATURE
<222> LOCATION: (5)..(5)
<223> OTHER INFORMATION: Xaa is amino-hexanoic acid
<220> FEATURE:
<221> NAME/KEY: MISC_FEATURE
<222> LOCATION: (8)..(8)
<223> OTHER INFORMATION: Xaa is amino-hexanoic acid
<220> FEATURE:
<221> NAME/KEY: MISC_FEATURE
<222> LOCATION: (17)..(17)
<223> OTHER INFORMATION: Xaa is D-Arg

<400> SEQUENCE: 65

Arg Xaa Arg Arg Xaa Arg Arg Xaa Arg Ile His Ile Leu Phe Gln Asn
1               5                   10                  15

Arg Arg Met Lys Trp His Lys
            20

<210> SEQ ID NO 66
<211> LENGTH: 29
<212> TYPE: PRT
<213> ORGANISM: Artificial Sequence
<220> FEATURE:
<223> OTHER INFORMATION: Synthetic peptide

<400> SEQUENCE: 66

Gly Arg Lys Lys Arg Arg Gln Arg Arg Arg Pro Pro Gln Lys Lys Gly
1               5                   10                  15

Arg Lys Gln Ser Gly Glu Ser Leu Gly Thr Pro Lys Lys
            20                  25

<210> SEQ ID NO 67
<211> LENGTH: 28
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MISC_FEATURE
<222> LOCATION: (2)..(2)
<223> OTHER INFORMATION: Xaa is amino-hexanoic acid
<220> FEATURE:
<221> NAME/KEY: MISC_FEATURE
<222> LOCATION: (5)..(5)
<223> OTHER INFORMATION: Xaa is amino-hexanoic acid
<220> FEATURE:
<221> NAME/KEY: MISC_FEATURE
<222> LOCATION: (8)..(8)
<223> OTHER INFORMATION: Xaa is amino-hexanoic acid
<220> FEATURE:
<221> NAME/KEY: MISC_FEATURE
<222> LOCATION: (11)..(11)
<223> OTHER INFORMATION: Xaa is amino-hexanoic acid

<400> SEQUENCE: 67

Arg Xaa Arg Arg Xaa Arg Arg Xaa Arg Arg Xaa Arg Lys Lys Ser Arg
1               5                   10                  15

Lys Glu Lys Lys Gln Thr Gly Ser Gly Pro Leu Gly
            20                  25

<210> SEQ ID NO 68
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is amino-hexanoic acid
<220> FEATURE:
<221> NAME/KEY: MISC_FEATURE
<222> LOCATION: (5)..(5)
<223> OTHER INFORMATION: Xaa is beta-Ala
<220> FEATURE:
<221> NAME/KEY: MISC_FEATURE
<222> LOCATION: (8)..(8)
<223> OTHER INFORMATION: Xaa is amino-hexanoic acid
<220> FEATURE:
<221> NAME/KEY: MISC_FEATURE
<222> LOCATION: (11)..(11)
<223> OTHER INFORMATION: Xaa is beta-Ala
<220> FEATURE:
<221> NAME/KEY: MISC_FEATURE
<222> LOCATION: (13)..(13)
<223> OTHER INFORMATION: Xaa is amino-hexanoic acid
<220> FEATURE:
<221> NAME/KEY: MISC_FEATURE
<222> LOCATION: (14)..(14)
<223> OTHER INFORMATION: Xaa is beta-Ala

<400> SEQUENCE: 68

Arg Xaa Arg Arg Xaa Arg Arg Xaa Arg Arg Xaa Arg Xaa Xaa Lys Lys
1               5                   10                  15

Ser Arg Lys Glu Lys Lys Gln Thr Gly Ser Gly Pro Leu Gly
            20                  25                  30

<210> SEQ ID NO 69
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is amino-hexanoic acid
<220> FEATURE:
<221> NAME/KEY: MISC_FEATURE
<222> LOCATION: (5)..(5)
<223> OTHER INFORMATION: Xaa is amino-hexanoic acid
```

```
<220> FEATURE:
<221> NAME/KEY: MISC_FEATURE
<222> LOCATION: (8)..(8)
<223> OTHER INFORMATION: Xaa is amino-hexanoic acid
<220> FEATURE:
<221> NAME/KEY: MISC_FEATURE
<222> LOCATION: (17)..(17)
<223> OTHER INFORMATION: Xaa is D-Arg

<400> SEQUENCE: 69

Arg Xaa Arg Arg Xaa Arg Arg Xaa Arg Ile His Ile Leu Phe Gln Asn
1               5                   10                  15

Arg Arg Met Lys Trp His Lys Lys Ser Arg Lys Glu Lys Lys Gln
            20                  25                  30

Thr Gly Ser Gly Pro Leu Gly
            35

<210> SEQ ID NO 70
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is amino-hexanoic acid
<220> FEATURE:
<221> NAME/KEY: MISC_FEATURE
<222> LOCATION: (5)..(5)
<223> OTHER INFORMATION: Xaa is amino-hexanoic acid
<220> FEATURE:
<221> NAME/KEY: MISC_FEATURE
<222> LOCATION: (8)..(8)
<223> OTHER INFORMATION: Xaa is amino-hexanoic acid
<220> FEATURE:
<221> NAME/KEY: MISC_FEATURE
<222> LOCATION: (17)..(17)
<223> OTHER INFORMATION: Xaa is D-Arg

<400> SEQUENCE: 70

Arg Xaa Arg Arg Xaa Arg Arg Xaa Arg Ile His Ile Leu Phe Gln Asn
1               5                   10                  15

Arg Arg Met Lys Trp His Lys Lys Arg Phe Arg Lys Glu Lys Lys Gln
            20                  25                  30

Leu Gly Ser Gly Leu Leu Gly
            35

<210> SEQ ID NO 71
<211> LENGTH: 28
<212> TYPE: PRT
<213> ORGANISM: Artificial Sequence
<220> FEATURE:
<223> OTHER INFORMATION: Synthetic peptide

<400> SEQUENCE: 71

Gly Arg Lys Lys Arg Arg Gln Arg Arg Arg Pro Pro Gln Ser Gly Pro
1               5                   10                  15

Pro Cys Lys Lys Ser Arg Lys Glu Lys Lys Gln Thr
            20                  25

<210> SEQ ID NO 72
<211> LENGTH: 28
<212> TYPE: PRT
<213> ORGANISM: Artificial Sequence
<220> FEATURE:
<223> OTHER INFORMATION: Synthetic peptide
```

```
<400> SEQUENCE: 72

Gly Arg Lys Lys Arg Arg Gln Arg Arg Pro Pro Gln Pro Cys Lys
1               5                   10                  15

Lys Ser Arg Lys Glu Lys Lys Gln Thr Gly Ser Gly
                20                  25

<210> SEQ ID NO 73
<211> LENGTH: 28
<212> TYPE: PRT
<213> ORGANISM: Artificial Sequence
<220> FEATURE:
<223> OTHER INFORMATION: Synthetic peptide

<400> SEQUENCE: 73

Gly Arg Lys Lys Arg Arg Gln Arg Arg Pro Pro Gln Lys Ser Arg
1               5                   10                  15

Lys Glu Lys Lys Gln Thr Gly Ser Gly Pro Leu Gly
                20                  25

<210> SEQ ID NO 74
<211> LENGTH: 28
<212> TYPE: PRT
<213> ORGANISM: Artificial Sequence
<220> FEATURE:
<223> OTHER INFORMATION: Synthetic peptide

<400> SEQUENCE: 74

Gly Arg Lys Lys Arg Arg Gln Arg Arg Pro Pro Gln Lys Glu Lys
1               5                   10                  15

Lys Gln Thr Gly Ser Gly Pro Leu Gly Asn Ser Tyr
                20                  25

<210> SEQ ID NO 75
<211> LENGTH: 27
<212> TYPE: PRT
<213> ORGANISM: Artificial Sequence
<220> FEATURE:
<223> OTHER INFORMATION: Synthetic peptide

<400> SEQUENCE: 75

Gly Arg Lys Lys Arg Arg Gln Arg Arg Pro Pro Gln Ser Arg Lys
1               5                   10                  15

Glu Lys Lys Gln Thr Gly Ser Gly Pro Leu Gly
                20                  25

<210> SEQ ID NO 76
<211> LENGTH: 22
<212> TYPE: PRT
<213> ORGANISM: Artificial Sequence
<220> FEATURE:
<223> OTHER INFORMATION: Synthetic peptide

<400> SEQUENCE: 76

Gly Arg Lys Lys Arg Arg Gln Arg Arg Pro Pro Gln Lys Ser Arg
1               5                   10                  15

Lys Glu Lys Lys Gln Thr
                20
```

INHIBITORS OF APOPTOSIS AND USES THEREOF

RELATED PATENT APPLICATIONS

The present patent application is filed pursuant to 35 U.S.C. §371 as a U.S. National Phase Application of International Patent Application No. PCT/EP2011/070404, which was filed on Nov. 17, 2011, claiming the benefit of priority to International Patent Application No. PCT/IB2010/003158 filed on Nov. 18, 2010. The content of each of the aforementioned Patent Applications is incorporated herein by reference in its entirety.

FIELD OF THE INVENTION

The invention relates to inhibitors of apoptosis and to their uses, in particular in medical treatments.

BACKGROUND OF THE INVENTION

Coronary heart disease is the leading cause of death worldwide, accounting for 3.8 million deaths in men and 3.4 million deaths in women annually. As the population grows older and comorbidities (e.g., obesity and metabolic syndrome) become more prevalent, as in recent years, the enormous public health burden caused by ischemic heart disease is likely to increase even further (reviewed in Yellon et al, N Engl J Med, 2007; 357: 1121-1135).

Coronary heart disease refers to the failure of coronary circulation to provide adequate blood supply to cardiac muscle and surrounding tissue. The most common cause of coronary heart disease is the accumulation of atheromatous plaques (i.e., fatty deposits) within the walls of coronary arteries. Occlusion of a coronary artery limits blood flow to the heart, leads to ischemia of the myocardial cells (i.e., cell starvation secondary to a lack of oxygen) and may result in myocardial cell death, which is called myocardial infarction (MI) or acute myocardial infarction (AMI)—commonly known as a heart attack. AMI is the leading cause of death in both Europe and the United States, and remains a frequent (more than 1.5 million new cases per year in the United States) and disabling (leading to heart failure) disease. Infarct size is a major determinant of myocardial functional recovery and mortality after AMI. Currently, the most effective way to limit infarct size is to reperfuse the jeopardized myocardium as soon as possible with the use of coronary angioplasty or thrombolysis and to prevent reocclusion of the coronary artery with the use of antiplatelet therapy. Reperfusion, or restoration of blood flow to the ischemic myocardium, is achieved with thrombolytic therapy that dissolves the thrombus or through dilatation of the occluded artery by percutaneous coronary angioplasty. Reperfusion is necessary for the salvage of myocardial cells and cardiac function in general. However, reperfusion initiates a cascade of events that leads to "reperfusion injury". This also occurs following recovery from cardioplegic arrest of the heart during bypass surgery. Reperfusion injury is characterized by arrhythmias, endothelial dysfunction leading to the noreflow phenomenon and myocardial stunning (reversible loss of myocardial contractility).

Reperfusion injury culminates in apoptotic death of cardiac cells that were viable immediately before myocardial reperfusion. The involvement of a highly-regulated form of cell death during myocardial ischemia/reperfusion may lead to novel therapeutic interventions in the reperfusion phase. However, the apoptosis signalling pathways that are involved during myocardial ischemia/reperfusion have not yet been fully delineated in vivo.

Finding new treatments for inhibiting apoptosis (i.e., "programmed cell death"), and in particular for treating myocardial infarction and reperfusion injury, thus constitutes a real challenge to protect cardiac function and to save lives.

SUMMARY OF THE INVENTION

The invention is based on the finding that it is possible to decrease apoptosis of cardiac cells after myocardial infarction by inhibiting the Fas signalling pathway. The Fas Receptor trimerizes upon binding to the FasL (Fas Ligand) and induces apoptosis through a cytoplasmic domain called DD (Death Domain) that interacts with signalling adaptors such as FAF-1 (Fas-Associated Factor-1), FADD (Fas-Associated Death Domain), DAXX (Death-Domain Associated protein), FAP-1, FLASH (FLICE-associated huge) and RIP (Receptor-Interacting Protein). DAXX and FADD independently bind to Fas, and activate distinct apoptotic pathways. DAXX can enhance Fas-mediated apoptosis by activating the JNK kinase cascade, culminating in phosphorylation and activation of transcription factors such as c-Jun. In contrast, FADD triggers, through a cascade of signalling caspases, the release of mitochondrial pro-apoptotic factors like CytoC (Cytochrome-C) and SMAC (Second Mitochondria-derived Activator of Caspases) also called Diablo.

The inventors have shown that inhibiting the interaction of the Fas Receptor with DAXX (SEQ ID NO: 1) or with FADD (SEQ ID NO: 8) leads to a strong decrease in the apoptosis of cardiac cells after myocardial infarction. Furthermore, the present inventors have unexpectedly found that small fragments of DAXX and of FADD retain the anti-apoptotic ability of the full proteins DAXX and FADD, respectively.

Accordingly, the present invention relates to a peptide consisting of:

a fragment of 16, 17, 18, 19, 20, 21, 22, 23 or 24 consecutive amino acid residues of the DAXX protein of SEQ ID NO: 1, wherein said fragment comprises the amino acid sequence set forth in SEQ ID NO: 5, or a fragment of 9, 10, 11, 12, 13, 14, 15, 16 or 17 consecutive amino acid residues of the FADD protein of SEQ ID NO: 8, wherein said fragment comprises the amino acid sequence set forth in SEQ ID NO: 12, wherein said peptide is capable of inhibiting cell apoptosis.

In certain embodiments, an anti-apoptotic peptide according to the invention is a DAXX protein fragment consisting of the amino acid sequence set forth in SEQ ID NO: 5. In other embodiments, an anti-apoptotic peptide is a DAXX fragment consisting of the amino acid sequence set forth in any one of SEQ ID NOs: 21-44.

In other embodiments, an anti-apoptotic peptide according to the invention is a FADD protein fragment consisting of the amino acid sequence set forth in SEQ ID NO: 12 or SEQ ID NO: 9. In other embodiments, an anti-apoptotic peptide is a FADD fragment consisting of the amino acid sequence set forth in any one of SEQ ID NOs: 45-57.

In another aspect, the present invention relates to a peptidomimetic of an anti-apoptotic peptide according to the invention.

In yet another aspect, the present invention provides a conjugate comprising an anti-apoptotic peptide or a peptidomimetic according to the invention linked to a Cell Penetrating Peptide. The Cell Penetrating Peptide may be Tat, RXR, Bpep or Pip2b.

In certain embodiments, the Cell Penetrating Peptide is linked to the peptide or to the peptidomimetic through a linker.

In certain embodiments, the Cell Penetrating Peptide is selected from the group consisting of Tat, RXR, Bpep and Pip2b.

In particular, in certain preferred embodiments, the conjugate consists of the amino acid sequence set forth in SEQ ID NO: 58, SEQ ID NO: 59, SEQ ID NO: 60 or SEQ ID NO: 61.

In yet another aspect, the present invention relates to a pharmaceutical composition comprising at least one pharmaceutically acceptable carrier or excipient and an effective amount of at least one peptide, or at least one peptidomimetic or at least one conjugate according to the invention.

In certain embodiments, a pharmaceutical composition according to the invention further comprises at least one additional biologically active agent. In particular, the biologically active agent may be selected from the group consisting of cyclosporine A, BH4, and combinations thereof.

In still another aspect, the present invention provides the peptides, peptidomimetics, conjugates and pharmaceutical compositions according to the invention for use in a method of treatment of the human or animal body, in particular for use in a method for inhibiting cell apoptosis in the human or animal body.

In certain embodiments, the peptides, peptidomimetics, conjugates and pharmaceutical compositions according to the invention are used in a method for the treatment of acute myocardial infarction (AMI), cerebral infarction, organ transplantations, cardiac interventions (extra-corporally circulation and temporary vessel occlusion), or acute circulation perturbations (state of shock), in the human or animal body.

In other embodiments, the peptides, peptidomimetics, conjugates and pharmaceutical compositions according to the invention are used in a method for treatment of ischemia, in particular cardiac ischemia, kidney ischemia, ischemic colitis, mesenteric ischemia, brain ischemia, limb ischemia or skin ischemia, in the human or animal body.

In yet other embodiments, the peptides, peptidomimetics, conjugates and pharmaceutical compositions according to the invention are used in a method for treatment of reperfusion injury in the human or animal body.

In a related aspect, the present invention also provides a method for treating a disease or condition associated with apoptosis in a subject, comprising a step of: administering to said subject an effective amount of at least one peptide, or at least one peptidomimetic, or at least one conjugate or at least one pharmaceutical composition according to the invention.

In certain embodiments, the method further comprise a step of administering to said subject at least one additional biologically active agent selected from the group consisting of cyclosporine A, BH4, and combinations thereof.

As mentioned above, in these methods of treatment, the disease or condition associated with apoptosis may be selected from the group consisting of acute myocardial infarction (AMI), cerebral infarction, organ transplantations, cardiac interventions, acute circulation perturbations, reperfusion injury, and ischemia.

These and other objects, advantages and features of the present invention will become apparent to those of ordinary skill in the art having read the following detailed description of the preferred embodiments.

BRIEF DESCRIPTION OF THE DRAWING

FIG. 1: Determination of the DAXX epitope by SPOT synthesis. (A) The amino acid sequence of DAXX was dissected in overlapping peptide arrays (pepscan; 15 mer peptides with a shift of 3 amino acids) and analyzed in enzyme-linked blot. The black rectangle shows the four brightest spots with the corresponding epitope sequence. Incubation conditions: His-tagged intracellular region of Fas receptor [10 µg/ml]; antibodies: anti-His-(mouse) (Sigma H1029; 1:6,000)/anti-mouse-HRP (Calbiochem 401207; 1:2,000), exposure time: 1 minute. (B) Alignment of the human DAXX sequence comprising the 16-mer KKSRKEKKQTGSGPLG (=DAXXp of SEQ ID NO: 5) with the DAXX sequences of other species (mouse, rat, dog (CANFA) and green monkey (CHLAE)).

FIG. 5: In vitro evaluation of the anti-apoptotic activity of CPPs and CPP-conjugates. Workflow and quantitation of DNA fragmentation in (A) C2C12 cells, (B) primary cardiomyocytes, (C) H9c2 cells and (D) NG108-15 cells. Data were normalized to 100% STS. Data shown are the means±SEM, with n≥5. Cells were seeded in 24-well plates and grown overnight. The next day, the cells were incubated with STS alone or with STS+1 µM peptide (in OPTI-MEM) (OPTI-MEM® is a modification of Eagle's Minimum Essential Media, buffered with HEPES and sodium bicarbonate, and supplemented with hypoxanthine, thymidine, sodium pyruvate, L-glutamine, trace elements, and growth factors) (STS concentration and incubation time for each cells are given in the figure). Thereafter, solutions were removed, replaced by complete medium and further incubated for 40 h. Following the regeneration phase, the cells were lyzed and DNA fragmentation was detected according to manufacturer's instructions (Cell Death detection ELISA$^{PLUS}$ kit—Roche Diagnostics).

FIG. 8: Determination of FADDp15 and its anti-apoptotic effect in cardiomyocytes. (A) The protein sequences of FADD were dissected in overlapping peptide arrays (pepscan; 15 mer peptides with a shift of 3 amino acids) and analyzed using enzyme-linked blot. The black rectangle shows the three brightest spots with the corresponding epitope sequences, spot numbers and signal intensities (BLU) provided below. (B) The peptide sequence of FADDp-11 (=FADDp15=SEQ ID NO: 9) was successively shortened by one amino acid residue at the C-terminus, the N-terminus, or at both the C-terminus and the N-terminus, and analyzed using enzyme-linked blot. The spots indicated with an arrow exhibited the highest signal intensities (BLU). The shortest FADD epitope (a 9-mer with sequence KRKLERVQS (=FADDp=SEQ ID NO: 12)) corresponded to spot No. 24. Incubation conditions: His-tagged intracellular region of Fas receptor [10 µg/ml]; antibodies: anti-His-(mouse) (Sigma H1029; 1:6,000)/anti-mouse-HRP (Calbiochem 401207; 1:2,000), exposure time: 1 minute.

FIG. 9: Comparison of FADDp constructs with Tat-DAXXp in terms of anti-apoptotic activity in primary cardiomyocytes and in H9c2 cells. Quantification of DNA normalized to 100% STS. Data shown are the means±SEM, with n≥5. Cells were seeded in 24-well plates and grown overnight. The next day, the cells were incubated with STS alone or with STS+1 µM peptide (in OPTI-MEM®) (OPTI-MEM® is a modification of Eagle's Minimum Essential Media, buffered with HEPES and sodium bicarbonate, and supplemented with hypoxanthine, thymidine, sodium pyruvate, L-glutamine, trace elements, and growth factors) (STS concentration is given in the figure and incubation time is given in FIG. 5). Thereafter, solutions were removed, replaced by complete medium and further incubated for 40 hours. Following the regeneration phase, the cells were lyzed and DNA fragmentation was detected according to manufacturer's instructions (Cell Death detection ELISA$^{PLUS}$ kit—Roche Diagnostics). The short Tat-FADDp sequence was found to be less effective than Tat-DAXXp, but the longer Tat-FADDp15 had equal (in H9c2) or increased anti-apoptotic effect (in primary cardiomyocytes).

FIG. 12: Cardioprotective effects of Tat-DAXXp (1 mg/kg—IV) in mice subjected to IR$_{60'}$. Infarct size (in % of area at risk) and internucleosomal DNA fragmentation determined by ELISA were quantified in mice subjected to IR$_{60'}$ and treated with Tat, Tat-DAXXp or Tat-scrDAXXp (1 mg/kg) as well as with DAXXp (10 mg/kg) (intravenous injection (IV) 5 minutes before reperfusion). Means±SEM were plotted for (A): Area at risk/LV mass (left ventricle), (B): Infarct size (in % of area at risk) and (C): (I/NI ratio) corresponding to the ratio of soluble nucleosome in the ischemic portion versus the non-ischemic portion of LV tissues. Statistical analysis was performed using One-way ANOVA with Neuman-Keuls post test for multiple comparisons (GraphPad Prism software). $P<0.05$, $P<0.01$ and $P<0.001$ versus Tat-DAXXp were noted *, , and * respectively. P=ns (not significant) for $P>0.05$.

FIG. 15: Dose response for Tat-DAXXp and DAXXp in mice subjected to $IR_{24h}$. Area at risk and infarct size (in % of area at risk) were measured in mice subjected to $IR_{24h}$ and treated by Tat (1 mg/kg), Tat-DAXXp (0.1, 1 and 10 mg/kg) or DAXXp (0.1, 1 and 10 mg/kg) injected intravenously 5 minutes before reperfusion. Means±SEM were plotted for (A): Area at risk/LV mass (left ventricle), (B): Infarct size (in % of area at risk); and (C): soluble nucleosomes (in ratio I/NI).

DEFINITIONS

Figure 2:
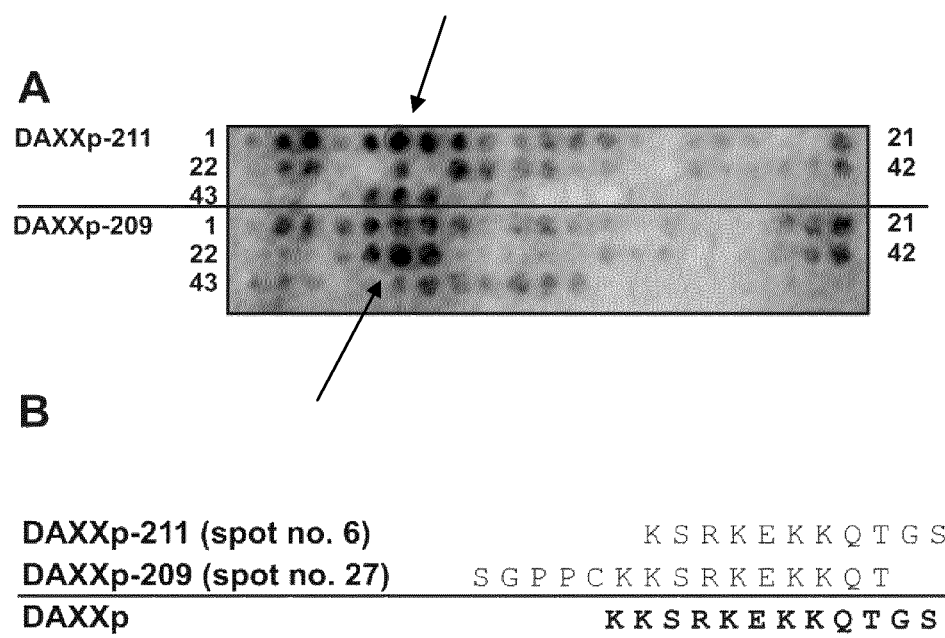
FIG. 2: Determination of the optimal length of the DAXX epitope (=DAXXp) by SPOT synthesis. (A) The DAXXp-211 and DAXXp-209 peptides (of SEQ ID NO: 2 and SEQ ID NO: 3, respectively) were successively shortened by one amino acid residue at the N-terminus, at the C-terminus and both at the N- and the C-termini, and analyzed using enzyme-linked blot. The spots indicated by an arrow exhibited the highest signal intensities (BLU). Incubation conditions: His-tagged intracellular region of Fas receptor [10 µg/ml]; antibodies: anti-His-(mouse) (Sigma H1029; 1:6, 000)/anti-mouse-HRP (Calbiochem 401207; 1:2,000), exposure time: 1 minute. (B) Alignment of both peptide sequences DAXXp-211 and DAXXp-209; corresponding to the brightest spots, to determine the optimal DAXX peptide sequence.
Figure 3:
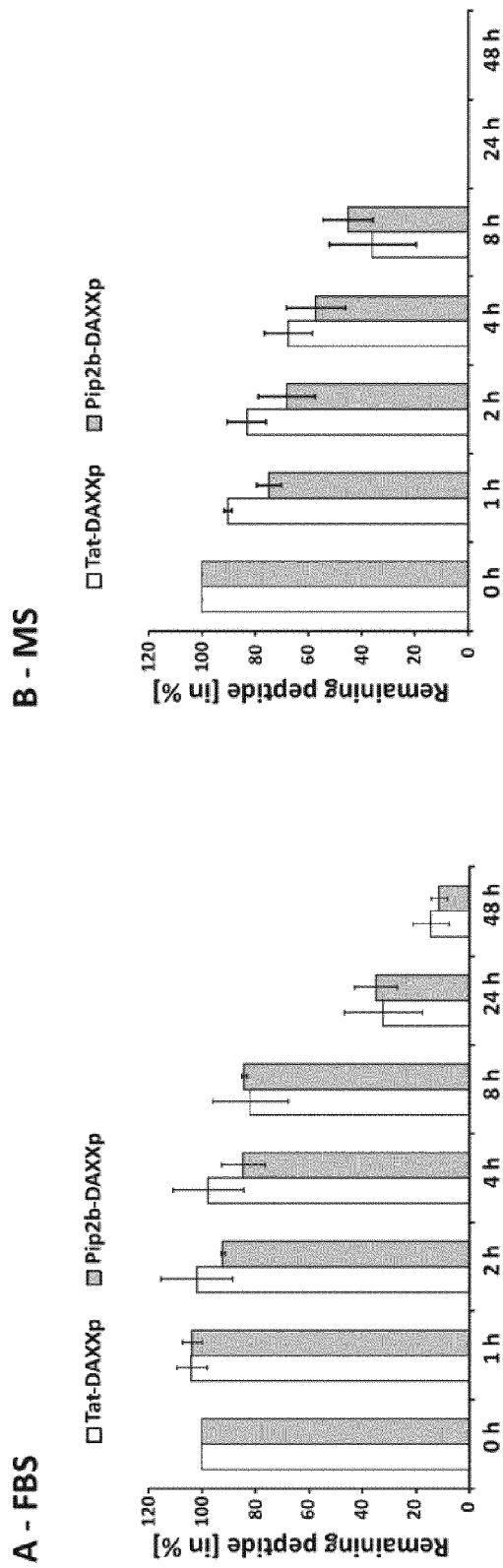
FIG. 3: Evaluation of Tat-DAXXp and Pip2b-DAXXp protease ability. (A) Stability measurements of Tat-DAXXp and Pip2b-DAXXp conjugates in fetal bovine serum (FBS, BioWest) and (B) freshly prepared mouse serum (MS). Peptides were incubated with 20% serum at 37° C. for 0 h, 1 h, 2 h, 4 h, 8 h, 24 h, and 48 h, and 50 µl of the incubation mixture was precipitated in 100 µl 10% dichloroacetic acid (DCA) in $H_2O/CH_3CN$ (50/50). The samples were mixed and kept at −20° C. The precipitated serum proteins were separated by centrifugation (14,000 rpm, 10 minutes) and the supernatant was analyzed by reverse-phase HPLC (measurement of the peak area in mV*sec). n≥2 for each condition. After a 2 h incubation in mouse serum, more than 70% of the peptides are still intact, whereas after 24 hours all the peptide are degraded.
Figure 4:
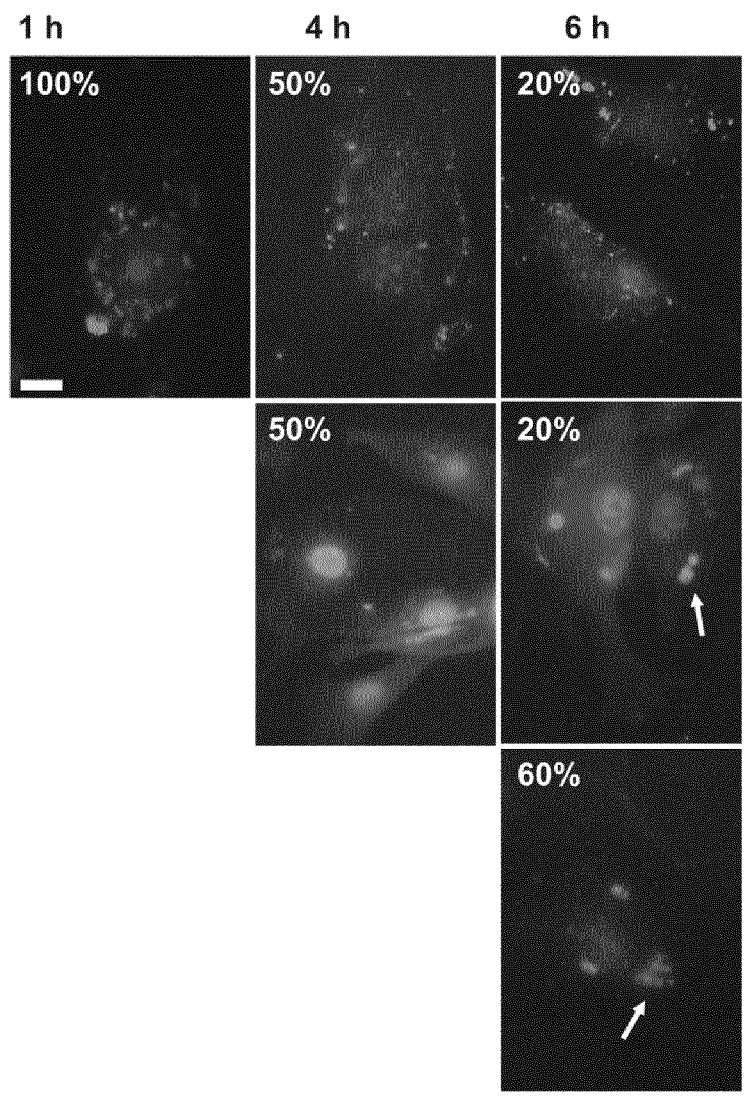
FIG. 4: Cellular distribution depends on incubation time. Primary cardiomyocytes were incubated with a 1 µM solution of CF-labeled Tat-DAXXp conjugates (green fluorescence) for 1 h, 4 h or 6 h. Cell nuclei were stained with Hoechst-dye (blue). White bars represent 10 µm. The intracellular distribution of CF-Tat-DAXXp after 1 h incubation revealed a punctuated pattern in the cytosol (which is characteristic of endosomal entrapment of the peptides after internalization via endocytosis) and no nuclear localization was detected. After 4 h incubation, CF-Tat-DAXXp seems to be able to escape from endosomal vesicles giving rise to a more diffuse labeling pattern. Moreover, a nucleus accumulation was observed. After a longer incubation time (6 hours), the CF-labelled peptide was encapsulated in large vesicles (white arrows) and eliminated from the cells.
Figure 6:
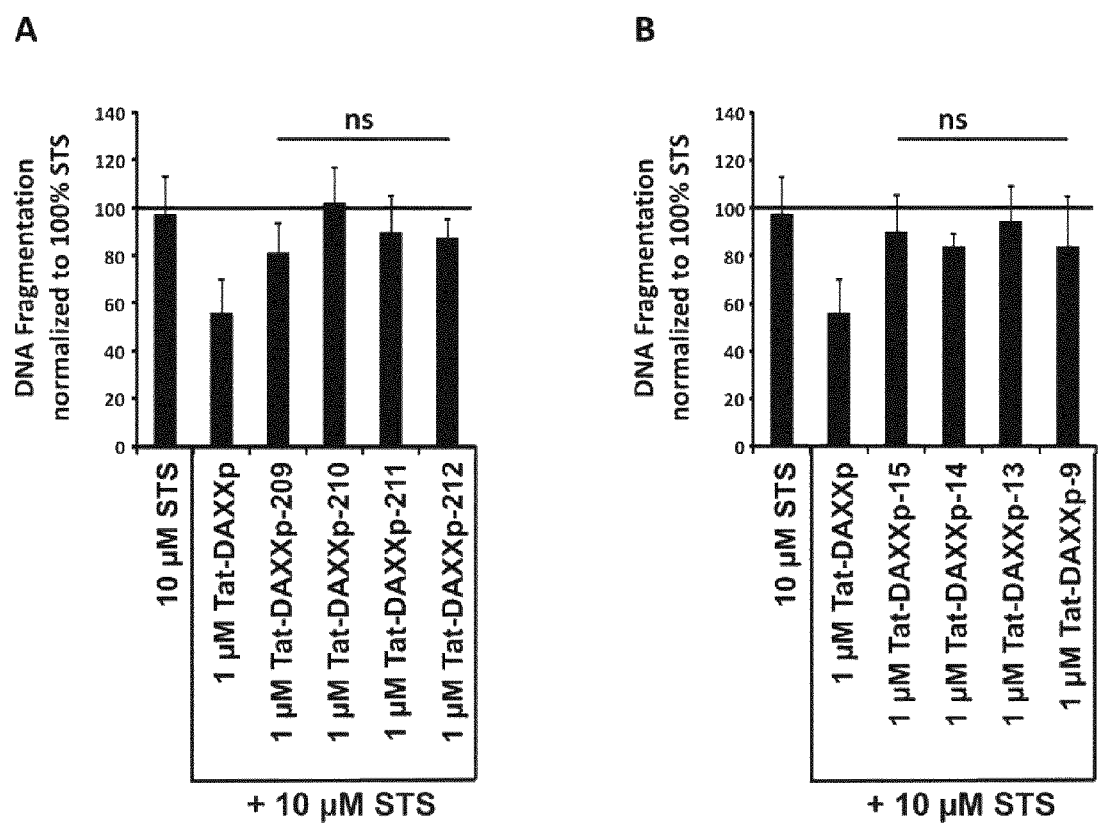
FIG. 6: Anti-apoptotic activity of variants of the Tat-DAXXp sequence on primary cardiomyocytes. As described in the caption of FIG. 5, the different analogues of the DAXXp sequence (see Table 2) were assessed for anti-apoptotic properties against STS (Cell Death detection ELISA$^{PLUS}$ kit—Roche Diagnostics) (A-B). None of the analogues were able to protect the primary cardiomyocytes—a fact which confirms that the 16mer DAXXp has the optimal length and sequence for highest cardioprotective effect.
Figure 7:
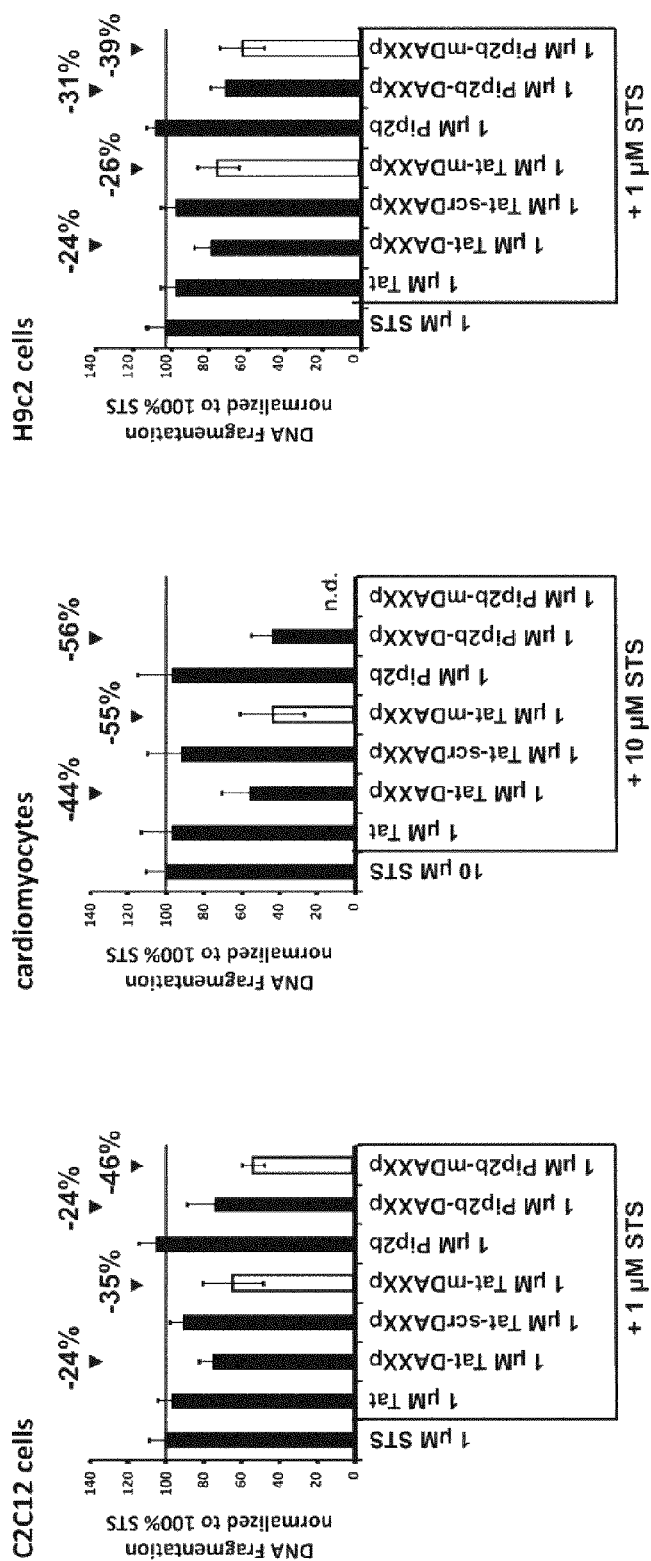
FIG. 7: Comparison of the murine/rat DAXXp with the human DAXXp sequence in terms of anti-apoptotic activity on C2C12 cells, primary cardiomyocytes, and H9c2. The murine DAXXp sequence conjugated to Tat (Tat-mDAXXp—SEQ ID NO: 61) which is identical to the rat DAXXp sequence (see FIG. 1B), was compared to the human construct (Tat-DAXXp) in terms of anti-apoptotic properties against STS (Cell Death detection ELISA$^{PLUS}$ kit—Roche Diagnostics). The C2C12 cells and the primary cardiomyocytes used were from mice and the H9c2 cells from rat. In all the cells, an increase in anti-apoptotic effect was observed using the murine Tat-mDAXXp sequence due to murine or rat cell types.
Figure 10:
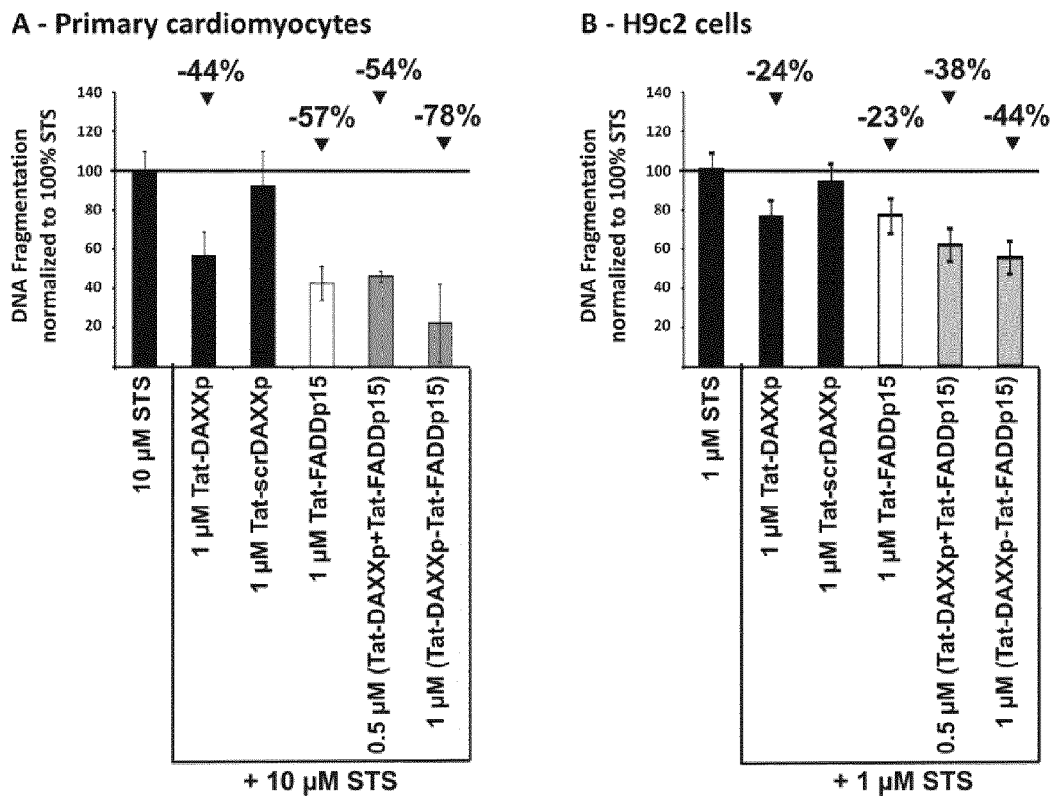
FIG. 10: Comparison of Tat-DAXXp and Tat-FADDp15 alone and in combination in primary cardiomyocytes (A) and in H9c2 cells (B). An incubation with both 0.5 µM Tat-DAXXp and 0.5 µM Tat-FADDp15 was found to result in the same or even higher anti-apoptotic effect when compared to the peptide alone at 1 µM. Furthermore, incubation with both peptides at 1 µM led to the highest protection in both cell types, suggesting that a combination of Tat-DAXXp and Tat-FADDp15 could be a promising application

Throughout the specification, several terms are employed that are defined in the following paragraphs.

The terms "protein", "polypeptide", and "peptide" are used herein interchangeably, and refer to amino acid sequences of a variety of lengths, either in their neutral (uncharged) forms or as salts, and either unmodified or modified by glycosylation, side chain oxidation, or phosphorylation. In certain embodiments, the amino acid sequence is a full-length native protein. However, in preferred embodiments, the amino acid sequence is a fragment of the full-length protein. In still other embodiments, the amino acid sequence is modified by additional substituents attached to the amino acid side chains, such as glycosyl units, lipids, or inorganic ions such as phosphates, as well as modifications relating to chemical conversion of the chains such as oxidation of sulfhydryl groups. Thus, the term "protein" (or its equivalent terms) is intended to include the amino acid sequence of the full-length native protein, or a fragment thereof, subject to those modifications that do not significantly change its specific properties. In particular, the term "protein" encompasses protein isoforms, i.e., variants that are encoded by the same gene, but that differ in their pI or MW, or both. Such isoforms can differ in their amino acid sequence (e.g., as a result of alternative splicing or limited proteolysis), or in the alternative, may arise from differential post-translational modification (e.g., glycosylation, acylation, phosphorylation).

The term "analog", when used herein in reference to a protein or polypeptide, refers to a peptide that possesses a similar or identical function as the protein or polypeptide but need not necessarily comprise an amino acid sequence that is similar or identical to the amino acid sequence of the protein or polypeptide or a structure that is similar or identical to that of the protein or polypeptide. Preferably, in the context of the present invention, an analog has an amino acid sequence that is at least 30%, more preferably, at least about: 35%, 40%, 45%, 50%, 55%, 60%, 65%, 70%, 75%, 80%, 85%, 90%, 95% or 99%, identical to the amino acid sequence of the protein or polypeptide. In certain preferred embodiments, an analog of a protein has an amino acid sequence that is at least 80% identical or at least 85% identical, preferably at least 90% identical, and most preferably at least 95% identical to the amino acid sequence of the protein.

The term "fragment", when used herein in reference to a protein or polypeptide, refers to a peptide comprising an amino acid sequence of at least 5 consecutive amino acid residues and of less than 30 consecutive amino acid residues of the protein or polypeptide, for example, of 7, 8, 9, 10, 11, 12, 13, 14, 15, 16, 17, 18, 19, 20, 21, 22, 23, 24 or 25 consecutive amino acid residues of the protein or polypeptide, preferably 9, 10, 11, 12, 13, 14, 15, 16, 17, 18, 19 or 20 consecutive amino acid residues of the protein or polypeptide, and more preferably 9, 10, 11, 12, 13, 14, 15, 16 or 17 consecutive amino acid residues of the protein or polypeptide. In the context of the present invention, a fragment of a protein or polypeptide retains the functional activity of the full length protein or polypeptide.

The term "homologous" (or "homology"), as used herein, is synonymous with the term "identity" and refers to the sequence similarity between two polypeptide molecules. When a position in both compared sequences is occupied by the same amino acid residue, then the respective molecules are homologous at that position. As used herein, the percentage of sequence identity refers to comparisons among amino acid sequences, and is determined by comparing two optimally aligned sequences over a comparison window, wherein the portion of the amino acid sequence in the comparison window may comprise additions or deletions (i.e., gaps) as compared to the reference sequence (which does not comprise additions or deletions) for optimal alignment of the two sequences. The percentage may be calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical amino acid residue occurs in both sequences or an amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., using the local homology algorithm of Smith and Waterman, 1981, Adv. Appl. Math. 2: 482, by the homology alignment algorithm of Needleman and Wunsch, 1970, J. Mol. Biol. 48:443, using the search for similarity method of Pearson and Lipman, 1988, Proc. Natl. Acad. ScL USA 85:2444, using computerized implementations of these algorithms (GAP, BESTFIT, FASTA, and TFASTA in the GCG Wisconsin Software Package), or using visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)). Examples of algorithms that are suitable for determining percent sequence identity and sequence similarity are the BLAST and BLAST 2.0 algorithms, which are described in Altschul et al., 1990, J. Mol. Biol. 215: 403-410 and Altschul et al., 1977, Nucleic Acids Res. 3389-3402, respectively.

Homologous amino acid sequences share identical or similar amino acid sequences. In the context of the present invention, similar residues are conservative substitutions for, or "allowed point mutations" of, corresponding amino acid residues in a reference sequence. "Conservative substitutions" of a residue in a reference sequence are substitutions that are physically or functionally similar to the corresponding reference residue, e.g., that have a similar size, shape, electric charge, chemical properties, including the ability to form covalent or hydrogen bonds, or the like. Particularly preferred conservative substitutions are those fulfilling the criteria defined for an "accepted point mutation" by Dayhoff et al. ("Atlas of Protein Sequence and Structure", 1978, Nat. Biomed. Res. Foundation, Washington, D.C., Suppl. 3, 22: 354-352).

In the context of the present invention, the term "treatment" is used to characterize a method that is aimed at delaying or preventing the onset of a disease or condition, at slowing down or stopping the progression, aggravation or deteriorations of the symptoms of the condition, at bringing about ameliorations of the symptoms of the condition, and/or at curing the condition. A treatment may be administered prior to the onset of the disease or condition, for a prophylactic or preventing action. Alternatively or additionally, it may be administered after initiation of the disease or condition, for a therapeutic action.

As used herein, the term "subject" refers to a human or animal, in particular a mammal (e.g., primate, dog, cat, goat, horse, pig, mouse, rat, rabbit and the like), that can be afflicted with a disease or condition associated with apoptosis, but may or may not have the disease or condition. In many embodiments of the present invention, the subject is a human being. In such embodiments, the subject is often referred to as an "individual". The term "individual" does not denote a particular age, and thus encompasses children, teenagers, and adult.

A "pharmaceutical composition" is defined herein as comprising an effective amount of a peptide of the invention, and at least one pharmaceutically acceptable carrier or excipient.

As used herein, the term "effective amount" refers to any amount of a peptide, compound, agent, or composition that is sufficient to fulfil its intended purpose(s), e.g., a desired biological or medicinal response in a cell, tissue, system or subject. For example, in certain embodiments of the present invention, the purpose(s) may be: to inhibit, prevent or decrease apoptosis, such as for example apoptosis associated with reperfusion injury or organ transplantation; and/or to prevent or treat a disease or condition associated with apoptosis.

The term "pharmaceutically acceptable carrier or excipient" refers to a carrier medium which does not interfere with the effectiveness of the biological activity of the active ingredient(s) and which is not significantly toxic to the host at the concentration at which it is administered. The term includes solvents, dispersion, media, coatings, antibacterial and antifungal agents, isotonic agents, and adsorption delaying agents, and the like. The use of such media and agents for pharmaceutically active substances is well known in the art (see for example "*Remington's Pharmaceutical Sciences*", E. W. Martin, 18$^{th}$ Ed., 1990, Mack Publishing Co.: Easton, Pa., which is incorporated herein by reference in its entirety).

DETAILED DESCRIPTION OF CERTAIN PREFERRED EMBODIMENTS

As mentioned above, the present invention relates to peptides with anti-apoptotic properties that are useful as therapeutic agents in the treatment and/or prevention of a large variety of diseases or conditions associated with apoptosis.

Peptides Inhibiting Cell Apoptosis

The peptides of the invention include DAXX fragments and FADD fragments that exhibit anti-apoptotic activity.

The terms "DAXX" and "DAXX protein" are used herein interchangeably. They refer to the protein called death-associated protein 6 which, in humans, is encoded by the DAXX gene (RefSeq (mRNA): NM_001141969.1) located at position 21.3 on the short arm (p) of chromosome 6. In preferred embodiments, DAXX has the amino acid sequence set forth in SEQ ID NO: 1. However, the DAXX protein may be an isoform of the DAXX protein of SEQ ID NO: 1 and may therefore have any amino acid sequence that is encoded by the human DAXX gene.

The terms "FADD" and "FADD protein" are used herein interchangeably. They refer to the protein called Fas-Associated protein with Death Domain which, in humans, is encoded by the FADD gene (RefSeq (mRNA): NM_003824.3) located at position 13.3 on the long arm (q) of chromosome 11. In preferred embodiments, FADD has the amino acid sequence set forth in SEQ ID NO: 8. However, the FADD protein may be an isoform of the FADD protein of SEQ ID NO: 8 and may therefore have any amino acid sequence that is encoded by the human FADD gene.

The inventors have shown that peptides consisting of an amino acid sequence set forth in SEQ ID NO: 5 ("DAXXp"), in SEQ ID NO: 6 ("DAXXp-14") or in SEQ ID NO: 2 ("DAXXp-15"="DAXXp-211"), which are all fragments of the DAXX protein (SEQ ID NO:1), interact with the Fas receptor, but that only DAXXp is capable of decreasing cell apoptosis. Similarly, the inventors have found that peptides consisting of an amino acid sequence set forth in SEQ ID NO: 9 ("FADDp15") and SEQ ID NO: 12 ("FADDp"), which are both fragments of the FADD protein (SEQ ID NO: 8), interact with the Fas receptor and decrease cell apoptosis.

Thus, in a particular embodiment, the anti-apoptotic peptide according to the invention is a DAXX fragment of 16 consecutive amino acid residues consisting of SEQ ID NO:

5. In another particular embodiment, the anti-apoptotic peptide according to the invention is a DAXX fragment of 17, 18, 19, 20, 21, 22, 23 or 24 consecutive amino acid residues comprising the amino acid sequence set forth in SEQ ID NO: 5. Preferably, such an anti-apoptotic peptide has an amino acid sequence selected from the group consisting of

```
(KKSRKEKKQTGSGPLGN),             SEQ ID NO: 17

(KKSRKEKKQTGSGPLGNS),            SEQ ID NO: 18

(KKSRKEKKQTGSGPLGNSY),           SEQ ID NO: 19

(KKSRKEKKQTGSGPLGNSYV),          SEQ ID NO: 20

(CKKSRKEKKQTGSGPLG),             SEQ ID NO: 21

(PCKKSRKEKKQTGSGPLG),            SEQ ID NO: 22

(PPCKKSRKEKKQTGSGPLG),           SEQ ID NO: 23

(GPPCKKSRKEKKQTGSGPLG),          SEQ ID NO: 24

(SGPPCKKSRKEKKQTGSGPLG),         SEQ ID NO: 25

(CKKSRKEKKQTGSGPLGN),            SEQ ID NO: 26

(CKKSRKEKKQTGSGPLGNS),           SEQ ID NO: 27

(CKKSRKEKKQTGSGPLGNSY),          SEQ ID NO: 28

(CKKSRKEKKQTGSGPLGNSYV),         SEQ ID NO: 29

(PCKKSRKEKKQTGSGPLGN),           SEQ ID NO: 30

(PCKKSRKEKKQTGSGPLGNS),          SEQ ID NO: 31

(PCKKSRKEKKQTGSGPLGNSY),         SEQ ID NO: 32

(PCKKSRKEKKQTGSGPLGNSYV),        SEQ ID NO: 33

(PPCKKSRKEKKQTGSGPLGN),          SEQ ID NO: 34

(PPCKKSRKEKKQTGSGPLGNS),         SEQ ID NO: 35

(PPCKKSRKEKKQTGSGPLGNSY),        SEQ ID NO: 36

(PPCKKSRKEKKQTGSGPLGNSYV),       SEQ ID NO: 37

(GPPCKKSRKEKKQTGSGPLGN),         SEQ ID NO: 38

(GPPCKKSRKEKKQTGSGPLGNS),        SEQ ID NO: 39

(GPPCKKSRKEKKQTGSGPLGNSY),       SEQ ID NO: 40

(GPPCKKSRKEKKQTGSGPLGNSYV),      SEQ ID NO: 41

(SGPPCKKSRKEKKQTGSGPLGN),        SEQ ID NO: 42

(SGPPCKKSRKEKKQTGSGPLGNS),       SEQ ID NO: 43
and (SGPPCKKSRKEKKQTGSGPLGNSY).      SEQ ID NO: 44
```

In a particular embodiment, the anti-apoptotic peptide according to the invention is a FADD fragment of 9 consecutive amino acid residues consisting of SEQ ID NO: 12. In another particular embodiment, the anti-apoptotic peptide according to the invention is a FADD fragment of 15 consecutive amino acid residues consisting of SEQ ID NO: 9. In yet other particular embodiments, the anti-apoptotic peptide according to the invention is a FADD fragment of 9, 10, 11, 12, 13, 14, 15, 16 or 17 consecutive amino acid residues comprising SEQ ID NO: 12. Preferably, such an anti-apoptotic peptide has an amino acid sequence selected from the group consisting of:

```
(KRKLERVQSG),      SEQ ID NO: 45

(KRKLERVQSGL),     SEQ ID NO: 46

(KRKLERVQSGLD),    SEQ ID NO: 47

(KRKLERVQSGLDL),   SEQ ID NO: 48

(RKRKLERVQS),      SEQ ID NO: 49

KRKRKLERVQS),      SEQ ID NO: 50

(GKRKLERVQSG),     SEQ ID NO: 51

(GKRKLERVQSGL),    SEQ ID NO: 52

(GKRKLERVQSGLD),   SEQ ID NO: 53

(GKRKLERVQSGLDL),  SEQ ID NO: 54

(VGKRKLERVQSG),    SEQ ID NO: 55

(VGKRKLERVQSGL),   SEQ ID NO: 56
and (VGKRKLERVQSGLD).  SEQ ID NO: 57
```

As mentioned above, in certain embodiments, the DAXX protein is an isoform of the DAXX protein of SEQ ID NO: 1. In such embodiments, the anti-apoptotic peptide according to the invention may be the DAXX fragment of 16 consecutive amino acid residues which corresponds to the fragment of SEQ ID NO: 5 in the DAXX protein of SEQ ID NO: 1.

Similarly, as mentioned above, in certain embodiments, the FADD protein is an isoform of the FADD protein of SEQ ID NO: 8. In such embodiments, the anti-apoptotic peptide according to the invention may be the FADD fragment of 9 consecutive amino acid residues which corresponds to the fragment of SEQ ID NO: 12 in the FADD protein of SEQ ID NO: 8; or may be the FADD fragment of 15 consecutive amino acid residues which corresponds to the fragment of SEQ ID NO: 9 in the FADD protein of SEQ ID NO: 8.

The DAXX isoforms and FADD isoforms preferably have an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or more than 99% identity with SEQ ID NO: 1 and SEQ ID NO: 8, respectively, and more preferably at least 95%, 96%, 97%, 98%, 99% or more than 99% identity with SEQ ID NO: 1 and SEQ ID NO: 8, respectively.

The peptides according to the invention, as well as the derivatives and conjugates thereof (see below), are able to inhibit, prevent and/or decrease cell apoptosis, in particular cardiomyocyte apoptosis. This ability can be assessed using any suitable method known by the skilled person, such as for example using a cell apoptosis detection kit. An example of a kit suitable for measuring cell apoptosis is the Cell Death Detection ELISA$^{PLUS}$® kit (Cat. No. 11 774 425 001, Roche Applied Science).

Derivatives of the Peptides According to the Invention

The invention also relates to biologically active derivatives of the peptides according to the invention. By "biologically active derivative" is meant any derivative of a peptide of the invention that retains the ability of the peptide to inhibit, prevent or decrease cell apoptosis.

In certain embodiments, a biologically active derivative has the amino acid sequence of an anti-apoptotic peptide of the invention that has been chemically and/or biologically modified.

Examples of derivatives are peptides according to the invention wherein:

at least one amino acid residue of the peptide has been substituted or deleted, at least one additional amino acid residue has been inserted into the peptide, and/or at least one amino acid residue of the peptide has been chemically altered or derivatized.

Preferably, a biologically active derivative according to the invention comprises only one or only two amino acid residue modifications selected from the group consisting of substitutions, insertions, deletions, alterations or derivatizations. In certain preferred embodiments, a biologically active derivative contains one conservative substitution, or two conservative substitutions. In certain preferred embodiments, a derivative of a DAXX fragment according to the invention exhibits one or two modifications that affect amino acid residues that are outside of SEQ ID NO: 5 (i.e., that are not comprised within SEQ ID NO: 5); and a derivative of a FADD fragment according to the invention exhibits one or two modifications that affect amino acid residues that are outside of SEQ ID NO: 12 (i.e., that are not comprised within SEQ ID NO: 12).

Suitable "chemically altered or derivatized" amino acids include, for example, naturally occurring amino acid derivatives, for example 4-hydroxyproline for proline, 5-hydroxylysine for lysine, homoserine for serine, ornithine for lysine, and the like. Other "chemically altered or derivatized" amino acids include amino acids that are attached to e.g., a label, such as fluorescein, tetramethylrhodamine or cyanine dye Cy5.5; or amino acid residues with one or more post-translational modifications such as acetylation, amidation, formylation, hydroxylation, methylation, phosphorylation, sulfatation, glycosylation or lipidation. Indeed, certain chemical modifications, in particular N-terminal glycosylation, have been shown to increase the stability of peptides in human serum (Powell et al, Pharma Res 1993: 10:1268-1273). "Chemically altered or derivatized" amino acids also include those with increased membrane permeability obtained by N-myristoylation (Brand, et al, Am J Physiol Cell Physiol 1996; 270:C1362-C1369).

Other derivatives of the peptides according to the invention are peptidomimetics of said peptides. Peptidomimetics refer to synthetic chemical compounds, which have substantially the same structural and/or functional characteristics of the peptides according to the invention. The mimetic can be entirely composed of synthetic, non-natural amino acid analogs, or can be a chimeric molecule including one or more natural amino acids and one or more non-natural amino acid analogs. The mimetic can also incorporate any number of natural amino acid conservative substitutions that do not destroy the mimetic's activity. Routine testing can be used to determine whether a mimetic has the requisite activity, using Test A according to the invention. The phrase "substantially the same", when used in reference to a mimetic or peptidomimetic, means that the mimetic or the peptidomimetic has one or more activities or functions of the referenced molecule, in particular inhibition of cell apoptosis. The techniques for developing peptidomimetics are conventional. For example, peptide bonds can be replaced by non-peptide bonds or non-natural amino acids that allow the peptidomimetic to adopt a similar structure, and therefore biological activity, to the original peptide. Further modifications can also be performed by replacing chemical groups of the amino acids with other chemical groups of similar structure. The development of peptidomimetics can be aided by determining the tertiary structure of the original fragment/peptide, either free or bound to the intracellular region of the Fas receptor, by NMR spectroscopy, crystallography and/or computer-aided molecular modeling. Once a potential peptidomimetic compound is identified, it may be synthesized and its ability to inhibit cell apoptosis can be assayed.

Peptidomimetics can contain any combination of non-natural structural components, which are typically from three structural groups: residue linkage groups other than the natural amine bond ("peptide bond") linkages; non-natural residues in place of naturally occurring amino acid residues; residues which induce secondary structural mimicry (e.g., beta turn, gamma turn, beta sheet, alpha helix conformation); or other changes which confer resistance to proteolysis. For example, lysine mimetics can be generated by reaction with succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitrobenzenesulfonic acid, O-methylisourea, 2,4-pentanedione, and transamidase-catalyzed reactions with glyoxylate.

One or more residues can also be replaced by an amino acid (or peptidomimetic residue) of the opposite chirality. Thus, any amino acid naturally occurring in the L-configuration (which can also be referred to as R or S, depending upon the structure of the chemical entity) can be replaced with the same amino acid or a mimetic, but of the opposite chirality, referred to as the D-amino acid, but which can additionally be referred to as the R- or S-form.

As will be appreciated by one skilled in the art, the peptidomimetics of the present invention can also include one or more of the modifications described herein for the "chemically altered or derivatized" amino acids, e.g., a label, or one or more post-translational modifications.

The peptides, derivatives and peptidomimetics can be produced and isolated using any method known in the art. Peptides can be synthesized, whole or in part, using usual chemical methods. Techniques for generating peptide and peptidomimetic libraries are well known, and include, for example, multipin, tea bag, split-couple-mix techniques and SPOT synthesis.

Conjugates

The invention also relates to conjugates comprising a peptide of the invention or a derivative thereof, linked to a Cell Penetrating Peptide or CPP.

Indeed, to facilitate the uptake of the peptides according to the invention, or derivatives thereof, across cell membranes, such as the plasma membrane of a cell, the inventors have shown that it is very useful to conjugate those peptides or derivatives thereof with "cell penetrating peptides" (CPPs). CPPs are well known peptides which can be conjugated to cargos to facilitate transport across the membranes. CPPs are for instance well described by Lebleu B. et al., Advanced Drug Delivery Reviews 60 (2008) 517-529 and by Said Hassane F. et al., Cell. Mol. Life Sci. (2010) 67:715-726. Any CPP can be used to improve the cytoplasmic delivery of fragments or derivatives thereof according to the invention.

Examples of CPPs which can be conjugated with the DAXX or FADD fragments, or derivatives thereof, according to the invention include, but are not limited to:

| Name | Sequence |
|---|---|
| Tat | GRKKRRQRRRPPQ |
| RXR | RXRRXRRXRRXR |
| Bpep | RXRRBRRXRRBRXB |
| Pip2b | RXRRXRRXRIHILFQNrRMKWHK | wherein:
  X=aminohexyl, β-alanyl, p-aminobenzoyl, isonipecotyl, or 4-aminobutyryl
  B=betaAlanine
  small letter=D-amino acid (D-amino acids may be replaced by L-amino acids).

A CPP typically has two or more cationic amino acids with hydrophobic amino acids or spacer groups separating some of the cationic amino acids. For example, the cationic amino acid is Arginine (R). Still typically, a CPP generally has at least 3 or 4 Arginine residues. In some embodiments the CPP contains 5, 6 or more Arginine residues.

The CPP is typically linked to the N-terminal or C-terminal end of the peptide or derivative thereof according to the invention, preferably to the C-terminal. Chemical linkage may be performed via any chemical bound such as for example a disulphide bond, thioether or thiol-maleimide linkage.

In a particular embodiment, the peptide or derivative thereof according to the invention is linked to the CPP through a linker. Any type of linker can be used by the skilled person, provided that said linker allows chemical linkage of the peptide or derivative thereof to the CPP. A variety of linkers are possible, including amino acid sequences having a C-terminal Cysteine residue that permits formation of a disulfide, thioether or thiol-maleimide linkage. Other ways of linking the peptide or derivative thereof according to the invention to the CPP include using of a C-terminal aldehyde to form an oxime. Still other linkers use the Click chemistry.

Examples of suitable linkers include, but are not limited to, amino acids or amino acid sequences chosen from the group consisting of: C, BC, XC, GC, BBCC, BXCC, XBC, X, XX, B, BB, BX and XB, wherein:
  X=aminohexyl, β-alanyl, p-aminobenzoyl, isonipecotyl, or 4-aminobutyryl
  B=betaAlanine.

Applications

The invention also relates to the peptides, derivatives thereof, and conjugates thereof, as described herein for use in a method of treatment of the human or animal body, and to the corresponding methods of treatment. More particularly, the invention concerns the peptides, derivatives thereof, and conjugates thereof for use in a method for treating a disease or condition associated with cell apoptosis and/or for inhibiting cell apoptosis in the human or animal body. The invention also provides methods for treating a disease or condition associated with cell apoptosis and/or for inhibiting cell apoptosis in a subject in need thereof, said methods comprising a step of administering to said subject an effective amount of a peptide according to the invention, a derivative thereof and/or a conjugate thereof. In certain embodiments, the subject is administered at least one anti-apoptotic DAXX-peptide according to the invention and at least one anti-apoptotic FADD-peptide according to the invention.

As used herein, the term "disease or condition associated with cell apoptosis" refers to any disease or clinical condition that is caused by, results in, or includes cell apoptosis. In certain embodiments, the disease or condition is associated with Fas receptor-mediated cell apoptosis. The term "disease or clinical condition associated with cell apoptosis" also encompasses any medical procedure that causes, results in or induces cell apoptosis and that is performed due to the presence of a disease or clinical condition in the subject.

Thus, the peptides, derivatives thereof, and conjugates thereof, and the methods of treatment according to the present invention may be used to treat acute myocardial infarction (AMI), cerebral infarction, or acute circulation perturbations (state of shock), in the human or animal body, and in particular to inhibit or decrease cell apoptosis associated with these diseases. The peptides, derivatives thereof, and conjugates thereof, and the methods of treatment according to the present invention may also be used to treat a subject undergoing organ transplantations (e.g., liver, heart, kidney, islet, and intestine grafts), cardiac interventions (reperfusion therapy, extra-corporally circulation, e.g. as cardiopulmonary bypass, and temporary vessel occlusion), and in particular to inhibit or decrease cell apoptosis caused by these medical procedures.

The peptides, derivatives thereof, and conjugates thereof, and the methods of treatment according to the present invention may be used for the treatment of ischemia, such as cardiac ischemia, kidney ischemia, ischemic colitis, mesenteric ischemia, brain ischemia, limb ischemia or skin ischemia, in the human or animal body, and in particular to inhibit or decrease cell apoptosis associated with ischemia.

The peptides, derivatives thereof, and conjugates thereof, and the methods of treatment according to the present invention may be used to treat a subject who is receiving or has received reperfusion, and in particular to inhibit or decrease cell apoptosis associated with reperfusion injury.

All the peptides, derivatives thereof, and conjugates thereof according to the present invention may be administered before and during ischemia, prior to, concurrently with or following reperfusion.

Apoptosis mediated by the Fas receptor has also been shown to be implicated in human liver diseases including viral hepatitis, Wilson's disease, alcoholic hepatitis, cholestatic liver disease, and in autoimmune disease (reviewed, for example, in Ehrenschwender et al., Adv. Exp. Med. Biol., 2009, 647: 64-93). Therefore, the peptides, derivatives thereof, and conjugates thereof, and the methods of treatment according to the present invention may also be used for the treatment of these diseases.

In the methods of treatment according to the invention, the peptides, the derivatives thereof or the conjugates thereof can be combined with other therapeutic agents, in particular agents employed in the treatment of apoptosis, ischemia, and/or reperfusion injury. In particular, combined treatments with agents targeting the intrinsic pathway of apoptosis, i.e. the mitochondrial pathway, are of great interest. Thus, in a related aspect, the present invention provides the peptides, the derivatives thereof, or the conjugates thereof in combination with other therapeutic agents, in particular agents employed in the treatment of apoptosis, ischemia, and/or reperfusion injury, for use in a method of treatment according to the invention. In one embodiment, the methods of treatment according to the invention also comprise a step of administering cyclosporine A and/or the BH4 peptide to said human or animal body. Indeed, cyclosporine A was shown to inhibit the mitochondrial PTP opening, and to decrease infarct size both in patients and in animal models of AMI (Gomez et al, Cardiovasc Res. 2009; 83(2):226-33; Piot et al, N Engl J Med. 2008; 359(5):473-81; Mewton al, J Am Coll Cardiol. 2010 Mar. 23; 55(12): 1200-5). BH4 derived from the antiapoptotic Bcl-xl protein has been reported to be efficient at decreasing apoptosis during ischemia-reperfusion when administered as a conjugate of Tat protein at the time of reperfusion (Ono et al, Eur J Cardiothorac *Surg.* 2005, 27(1): 117-121; Donnini et al, Cell Cycle 2009; 8(8):1271-1278; Boisguerin et al., J. Control Release, 2011, doi: 10.1016/j.jconrel.2011.07.037).

In the methods of treatment according to the invention, all the compounds (peptides, derivatives, conjugates, combined products) may be administered using any of a number of suitable routes, including but not limited to, intravenous, parenteral, intra-arterial, intramuscular, oral and nasal. Administration of a peptide of the invention, derivative thereof or conjugate thereof, will be in a dosage such that the amount administered is effective for the intended purpose. The route of administration, formulation (see below) and dosage administered will depend upon the therapeutic effect desired, the severity of the condition to be treated if already present, the presence of any infection, the age, sex, weight, and general health condition of the patient as well as upon the potency, bioavailability, and in vivo half-life of the peptide, derivative or conjugate used, the use (or not) of concomitant therapies, and other clinical factors. These factors are readily determinable by the attending physician in the course of the therapy.

A treatment according to the present invention may consist of a single dose or multiple doses. Thus, administration of a peptide, derivative or conjugate thereof, may be constant for a certain period of time, or periodic and at specific intervals, e.g., hourly, daily, weekly (or some other multiple day interval), etc. Alternatively, the administration may be continuous delivery for a period of time, e.g., intravenous delivery.

Pharmaceutical Compositions

As mentioned above, a peptide of the invention, a derivative thereof or conjugate thereof, may be administered per se or as a pharmaceutical composition. Accordingly, the present invention provides pharmaceutical compositions comprising an effective amount of at least one anti-apoptotic peptide of the invention (or a derivative thereof or conjugate thereof), and at least one pharmaceutically acceptable carrier or excipient. In some embodiments, the composition further comprises at least one additional biologically active agent. In certain embodiments, a pharmaceutical composition comprises at least one anti-apoptotic DAXX-peptide according to the invention and at least one anti-apoptotic FADD-peptide according to the invention.

A pharmaceutical composition according to the invention may be administered in any amount and using any route of administration effective for achieving the desired prophylactic and/or therapeutic effect. The optimal pharmaceutical formulation can be varied depending upon the route of administration and desired dosage. Such formulations may influence the physical state, stability, rate of in vivo release, and rate of in vivo clearance of the administered active ingredient(s).

The pharmaceutical compositions of the present invention may be formulated in dosage unit form for ease of administration and uniformity of dosage. The expression "unit dosage form", as used herein, refers to a physically discrete unit of at least one peptide of the invention (or at least one derivative thereof or conjugate thereof) and at least one pharmaceutically acceptable carrier or excipient. It will be understood, however, that the total daily dosage of the compositions will be decided by the attending physician within the scope of sound medical judgement.

Formulation.

Injectable preparations, for example, sterile injectable aqueous or oleaginous suspensions may be formulated according to the known art using suitable dispersing or wetting agents, and suspending agents. The sterile injectable preparation may also be a sterile injectable solution, suspension or emulsion in a non-toxic parenterally acceptable diluent or solvent, for example, as a solution in 2,3-butanediol. Among the acceptable vehicles and solvents that may be employed are water, Ringer's solution, U.S.P. and isotonic sodium chloride solution. In addition, sterile, fixed oils are conventionally employed as a solution or suspending medium. For this purpose any bland fixed oil can be employed including synthetic mono- or di-glycerides. Fatty acids such as oleic acid may also be used in the preparation of injectable formulations. Sterile liquid carriers are useful in sterile liquid form compositions for parenteral administration.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Liquid pharmaceutical compositions which are sterile solutions or suspensions can be administered by, for example, intravenous, intramuscular, intraperitoneal or subcutaneous injection. Injection may be via single push or by gradual infusion. Where necessary or desired, the composition may include a local anesthetic to ease pain at the site of injection.

In order to prolong the effect of an active ingredient, it is often desirable to slow the absorption of the ingredient from subcutaneous or intramuscular injection. Delaying absorption of a parenterally administered active ingredient may be accomplished by dissolving or suspending the ingredient in an oil vehicle. Injectable depot forms are made by forming micro-encapsulated matrices of the active ingredient in biodegradable polymers such as polylactide-polyglycolide. Depending upon the ratio of active ingredient to polymer and the nature of the particular polymer employed, the rate of ingredient release can be controlled. Examples of other biodegradable polymers include poly(orthoesters) and poly(anhydrides). Depot injectable formulations can also be prepared by entrapping the active ingredient in liposomes or microemulsions which are compatible with body tissues.

Liquid dosage forms for oral administration include, but are not limited to, pharmaceutically acceptable emulsions, microemulsions, solutions, suspensions, syrups, elixirs, and pressurized compositions. In addition to the active principle(s), the liquid dosage form may contain inert diluents commonly used in the art such as, for example, water or other solvent, solubilising agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cotton seed, ground nut, corn, germ, olive, castor, and sesame oils), glycerol, tetrahydrofurfuryl alcohol, polyethylene glycols, and fatty acid esters of sorbitan and mixtures thereof. Besides inert diluents, the oral compositions can also include adjuvants such as wetting agents, suspending agents, preservatives, sweetening, flavouring, and perfuming agents, thickening agents, colors, viscosity regulators, stabilizers or osmo-regulators. Examples of suitable liquid carriers for oral administration include water (potentially containing additives as above, e.g., cellulose derivatives, such as sodium carboxymethyl cellulose solution), alcohols (including monohydric alcohols and polyhydric alcohols such as glycols) and their derivatives, and oils (e.g., fractionated coconut oil and arachis oil). For pressurized compositions, the liquid carrier can be halogenated hydrocarbon or other pharmaceutically acceptable propellant.

Solid dosage forms for oral administration include, for example, capsules, tablets, pills, powders, and granules. In such solid dosage forms, an inventive peptide (or derivative thereof or conjugate thereof) may be mixed with at least one inert, physiologically acceptable excipient or carrier such as sodium citrate or dicalcium phosphate and one or more of: (a) fillers or extenders such as starches, lactose, sucrose, glucose, mannital, and silicic acid; (b) binders such as, for example, carboxymethylcellulose, alginates, gelatine, polyvinylpyrrolidone, sucrose, and acacia; (c) humectants such as glycerol; (d) disintegrating agents such as agar-agar, calcium carbonate, potato or tapioca starch, alginic acid, certain silicates, and sodium carbonate; (e) solution retarding agents such as paraffin; absorption accelerators such as quaternary ammonium compounds; (g) wetting agents such as, for example, cetyl alcohol and glycerol monostearate; (h) absorbents such as kaolin and bentonite clay; and (i) lubricants such as talc, calcium stearate, magnesium stearate, solid polyethylene glycols, sodium lauryl sulphate, and mixtures thereof. Other excipients suitable for solid formulations include surface modifying agents such as non-ionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. In the case of capsules, tablets and pills, the dosage form may also comprise buffering agents.

Solid compositions of a similar type may also be employed as fillers in soft and hard-filled gelatine capsules using such excipients as lactose or milk sugar as well as high molecular weight polyethylene glycols and the like. The solid dosage forms of tablets, dragees, capsules, pills, and granules can be prepared with coatings and shells such as enteric coatings, release controlling coatings and other coatings well known in the pharmaceutical formulating art. They may optionally contain opacifying agents and can also be of a composition such that they release the active ingredient(s) only, or preferably, in a certain part of the intestinal tract, optionally, in a delaying manner. Examples of embedding compositions which can be used include polymeric substances and waxes.

In certain embodiments, it may be desirable to administer an inventive anti-apoptotic peptide (or derivative thereof or conjugate thereof) locally in an area in need of treatment (e.g., the myocardium). This may be achieved, for example, and not by way of limitation, by local infusion during percutaneous coronary angioplasty or during coronay artery bypass surgery.

For topical administration, the pharmaceutical composition is preferably formulated as a gel, an ointment, a lotion, or a cream which can include carriers such as water, glycerol, alcohol, propylene glycol, fatty alcohols, triglycerides, fatty acid esters, or mineral oil. Other topical carriers include liquid petroleum, isopropyl palmitate, polyethylene glycol, ethanol (95%), polyoxyethylenemonolaurat (5%) in water, or sodium lauryl sulphate (5%) in water. Other materials such as antioxidants, humectants, viscosity stabilizers, and similar agents may be added as necessary.

In addition, in certain instances, it is expected that the inventive compositions may be disposed within transdermal devices placed upon, in, or under the skin. Such devices include patches, implants, and injections which release the active ingredient by either passive or active release mechanisms. Transdermal administrations include all administration across the surface of the body and the inner linings of bodily passage including epithelial and mucosal tissues. Such administrations may be carried out using the present compositions in lotions, creams, foams, patches, suspensions, solutions, and suppositories.

Materials and methods for producing various formulations are known in the art and may be adapted for practicing the subject invention. Suitable formulations for the delivery of antibodies can be found, for example, in "*Remington's Pharmaceutical Sciences*", E. W. Martin, 18$^{th}$ Ed., 1990, Mack Publishing Co.: Easton, Pa.

Additional Biologically Active Agents.

In certain embodiments, an inventive peptide is the only active ingredient in a pharmaceutical composition of the present invention. In other embodiments, the pharmaceutical composition further comprises one or more biologically active agents. Examples of suitable biologically active agents include, but are not limited to, anti-apoptotic agents, anti-inflammatory agents, immunomodulatory agents, analgesics, antimicrobial agents, antibacterial agents, antibiotics, antioxidants, antiseptic agents, and combinations thereof.

In certain embodiments, the additional biologically active agent is selected from the group consisting of cyclosporine A, BH4, and combinations thereof.

In such pharmaceutical compositions, the inventive anti-apoptotic peptide (or derivative thereof or conjugate thereof) and additional therapeutic agent(s) may be combined in one or more preparations for simultaneous, separate or sequential administration of the different components. More specifically, an inventive composition may be formulated in such a way that the peptide (or derivative thereof or conjugate thereof) and the therapeutic agent(s) can be administered together or independently from one another. For example, a peptide (or derivative thereof or conjugate thereof) and a therapeutic agent can be formulated together in a single composition. Alternatively, they may be maintained (e.g., in different compositions and/or containers) and administered separately.

EXAMPLES

The following examples describe some of the preferred modes of making and practicing the present invention. However, it should be understood that the examples are for illustrative purposes only and are not meant to limit the scope of the invention.

Synthesis of Membrane-Bound Inverted Peptide Arrays

The peptides were synthesized on N-modified CAPE-membranes (Bhargava et al, Mol. Recognit, 2002, 15: 145) and prepared by a MultiPep SPOT-robot (INTAVIS Bioanalytical Instruments AG, Cologne, Germany). Array design was performed with the aid of the in-house software LISA 1.71. The synthesis started with spot definition using a standard protocol [Frank, Tetrahedron, 1992, 48: 9217), followed by the coupling of a solution of Fmoc-cysteine-(Trt)-Opfp (0.3M) in N-methylpyrolidone (NMP) and Fmoc-alanine-Opfp (double coupling, 15 min reaction each). After Fmoc cleavage with piperidine in DMF (20%), 4-hydroxymethylphenoxyacetic acid (HMPA) dissolved in dimethylformamide (DMF, 0.6M solution) and activated with EEDQ (1.1 equiv) was added, and samples were directly spotted on the membrane (4× coupling, 15 min reaction each). The membrane was acetylated with acetic anhydride in DMF (2%), washed with DMF (5×3 min), ethanol (2×3 min), and diethyl ether (2×3 min), and finally air dried. Solutions of Fmoc-amino acid-OH (0.4M) activated with 1,1'-carbonyldiimidazole (CDI, 3 equiv) in DMF were spotted on the membrane (4× coupling, 15 min reaction time each). Proline, tyrosine, and glutamine were activated with 1,1'-carbonyldi(1,2,4-triazole) (CDT). The Fmoc group was removed from the spots, and the peptide sequences were completed using the standard SPOT synthesis protocol (Frank, Tetrahedron, 1992, 48: 9217) followed by a N-terminal tag with β-alanine.

For standard SPOT synthesis Fmoc-aa-Opfp were used with the following side chain protection: E-, D-(OtBu); C-, S-, T-, Y-(tBu); K-, W-(Boc); N-, Q-, H-(Trt); R-(Pbf). For thioether cyclization all peptides were N-acylated with bromoacetic acid 2,4-dinitrophenyl ester in DMF (1M), double coupling, 15 min reaction time each.

The membrane was washed with DMF (3×3 min) and dichloromethane (DCM, 3×3 min) and dried. To enable cyclization, the trityl side-chain protecting group of the cysteine was cleaved with trifluoroacetic acid (TFA, 7%), H$_2$O (2%) in DCM (1×5 min) followed by TFA (7%), TIBS (3%), H$_2$O (2%) in DCM. The membrane was washed with DCM (3×3 min), DMF (2×3 min), and DMF (2×3 min). The peptides were cyclized overnight by treatment with 25% aqueous Cs$_2$CO$_3$/DMF (1:1). The membrane was washed with DMF (2×3 min), H$_2$O (2×3 min), ethanol (2×3 min), and diethyl ether (2×3 min) and air-dried.

Hydrolysis and side-chain deprotection were achieved through one treatment with TFA (60%), TIBS (3%), and H$_2$O (2%) in DCM for 2.5 hours without shaking, followed by washing steps (DCM 3×3 min, DMF 3×3 min, ethanol 3×3 min, diethyl ether 2×3 min), followed by TFA (90%), TIBS (3%), and H$_2$O (2%) in DCM for 30 minutes without shaking. The membrane was washed with DCM (3×3 min), DMF (3×3 min), ethanol (2×3 min), phosphate buffer (pH 7.4, 0.1M, 2×3 min), H$_2$O (2×3 min), ethanol (2×3 min), and diethyl ether (2×3 min) and air dried.

Design and Delivery of Fragments According to the Invention

The primary sequence of the DAXX protein (SEQ ID NO: 1) was dissected in overlapping 15 mer peptides (3 amino acids shift) and all the peptides (243 peptides) were synthesized on cellulose membrane by SPOT synthesis as described above. The peptide library was incubated with the His-tagged intra-cellular region of the Fas receptor (Sigma). The interaction between Fas and the peptides was determined using a sandwich of anti-His(mouse)/anti-mouse-HRP and the signals were revealed using a LumiImager (Roche) as shown in FIG. 1A. Spot No. 211 (SEQ ID NO: 2) was found to display the highest signal intensity and spots Nos. 209, 210 and 212 (SEQ ID NO: 3, SEQ ID NO: 4 and SEQ ID NO: 7, respectively) were found to include the minimal epitope sequence (KSRKEKKQT).

Nevertheless, the sequence length analysis of the 15mer sequences KSRKEKKQTGSGPLG (spot 211, SEQ ID NO: 2) and SGPPCKKSRKEKKQT (spot 209, SEQ ID NO: 3) revealed that it is not possible to shorten the sequences arbitrarily to the minimal epitope found in FIG. 1. Using the SPOT synthesis as mentioned above, the influence of the peptide length was analyzed by shortening the given sequences at the N-terminus, the C-terminus and at both directions (FIG. 2A). The peptides sequences that showed the highest signal intensities are shown in FIG. 2B.

A merged combination of the highest signal intensity of the DAXXp-211 and of the DAXXp-209 which correspond to a 16mer peptide (KKSRKEKKQTGSGPLG), called the DAXX peptide or DAXXp (SEQ ID NO: 5) was performed. DAXXp was found to have an important in vitro and in vivo anti-apoptotic activity.

It is possible to elongate the peptide at the C-terminus in keeping with the fact that the dominant negative protein (DAXX-DN) [Roubille et al., Circulation, 2007; 116:2709-2717] encompasses a region extending from the DAXXp-211 peptide until the C-terminal end of the DAXX protein (FIG. 1B).

Applications in AMI

DAXXp peptides, conjugated or not to CPPs, have been tested for their anti-apoptotic activity in primary cardiomyocytes and for their ability to reduce infarct size in a mouse surgical I/R model after systemic administration.

In Vitro Evaluation

In a first step, the cellular uptake of the peptides listed in Table 1 was measured in primary cell culture of mouse cardiomyocytes using flow cytometry measurements (FACS—with CF-labeled peptides) and the absence of any cytotoxicity was verified.

TABLE 1

| CPPs, and CPP-DAXXp conjugates used in this study | | |
|---|---|---|
| Name | Sequence | AA |
| Tat | GRKKRRQRRRPPQ-NH2 (SEQ ID NO: 62) | 13 |
| (RXR)4 | (RXR)4-NH2 (SEQ ID NO: 63) | 12 |
| Bpep | RXRRBRRXRRBRXB-NH2 (SEQ ID NO: 64) | 14 |

TABLE 1-continued

CPPs, and CPP-DAXXp conjugates used in this study

| Name | Sequence | AA |
|---|---|---|
| Pip2b | (RXR)3-IHILFQNrRMKWHK-NH2 (SEQ ID NO: 65) | 23 |
| Tat-DAXXp | GRKKRRQRRRPPQ-KKSRKEKKQTGSGPLG-NH2 (=SEQ ID NO: 58) | 29 |
| Tat-ncDAXXp | GRKKRRQRRRPPQ-AKLYVYINELCTVLK-NH2 (ncDAXXp = SEQ ID NO: 13) | 29 |
| Tat-scrDAXXp | GRKKRRQRRRPPQ-KKGRKQSGESLGTPKK-NH2 (SEQ ID NO: 66) | 29 |
| (RXR)4-DAXXp | (RXR)4-KKSRKEKKQTGSGPLG-NH2 (SEQ ID NO: 67) | 28 |
| Bpep-DAXXp | RXRRBRRXRRBRXB-KKSRKEKKQTGSGPLG-NH2 (SEQ ID NO: 68) | 30 |
| Pip 2b-DAXXp | (RXR)3-IHILFQNrRMKWHK-KKSRKEKKQTGSGPLG-NH2 (SEQ ID NO: 69) | 39 |
| DAXXp | KKSRKEKKQTGSGPLG-NH2 (SEQ ID NO: 5) | 16 |
| Tat-DAXXp13 | GRKKRRQRRRPPQ-RKEKKQTGSGPLG-NH2 (DAXXp13 = SEQ ID NO: 14) | 26 |
| mDAXXp | KRFRKEKKQLGSGLLG-NH2 (SEQ ID NO: 15) | 16 |
| scrDAXXp | KKGRKQSGESLGTPKK -NH2 (SEQ ID NO: 16) | 16 |
| Tat-mDAXXp | GRKKRRQRRRPPQ-KRFRKEKKQLGSGLLG-NH2 (SEQ ID NO: 61) | 29 |
| Pip2b-mDAXXp | (RXR)3-IHILFQNrRMKWHK-KRFRKEKKQLGSGLLG-NH2 (SEQ ID NO: 70) | 39 |

X = amino-hexanoic acid; B = β-alanine, r = D-arginine; For FACS measurements, the peptides were N-teminally labeled with (5,6)-carboxyfluorescein (CF); all peptides are C-terminally amidated.
scr = scrambled version of DAXXp; mDAXXp is the mouse homolog of human DAXXp Other CPP-DAXXp derivatives that have been studied are presented in Table 2 below.

TABLE 2

Additional CPP-DAXXp derivates studied.

| | | |
|---|---|---|
| Tat-DAXXp | GRKKRRQRRRPPQ- | KKSRKEKKQTGSGPLG-NH2 (SEQ ID NO: 58) |
| Tat-DAXXp-209 | GRKKRRQRRRPPQ-SGPPCKKSRKEKKQT-NH2 (SEQ ID NO: 71) | |
| Tat-DAXXp-210 | GRKKRRQRRRPPQ- PCKKSRKEKKQTGSG-NH2 (SEQ ID NO: 72) | |
| Tat-DAXXp-211 | GRKKRRQRRRPPQ- KSRKEKKQTGSGPLG-NH2 (SEQ ID NO: 73) | |
| Tat-DAXXp-212 | GRKKRRQRRRPPQ- KEKKQTGSGPLGNSY-NH2 (SEQ ID NO: 74) | |
| Tat-DAXXp | GRKKRRQRRRPPQ-KKSRKEKKQTGSGPLG-NH2 (SEQ ID NO: 58) | |
| Tat-DAXXp-15 | GRKKRRQRRRPPQ-KSRKEKKQTGSGPLG-NH2 = Tat-DAXXp-211 (SEQ ID NO: 73) | |
| Tat-DAXXp-14 | GRKKRRQRRRPPQ- SRKEKKQTGSGPLG-NH2 (SEQ ID NO: 75) | |

TABLE 2-continued

Additional CPP-DAXXp derivates studied.

| Tat-DAXXp-13 | GRKKRRQRRRPPQ-RKEKKQTGSGPLG-NH2 (SEQ ID NO: 14) |
| Tat-DAXXp-9 | GRKKRRQRRRPPQ-KSRKEKKQT-NH2 (SEQ ID NO: 76) |

Additionally, the potential interaction of the fragments with the intracellular region of the Fas receptor was cross-validated by measuring the binding affinities (Kd) using the surface plasmon resonance (SPR) technique (*Biacore Life Science*, Sweden). Binding affinities of the fragment alone and in conjugation with the CPPs are summarized in Table 3.

TABLE 3

Measurement of the binding affinities (Kd, in µM) of the used constructs.

| Name | Sequence | Kd ± SD [µM] |
|---|---|---|
| DAXXp | KKSRKEKKQTGSGPLG-NH2 (SEQ ID NO: 5) | 333 ± 62 |
| mDAXXp | KRERKEKKQLGSGLLG-NH2 (SEQ ID NO: 15) | 252 ± 64 |
| scrDAXXp | KKGRKQSGESLGTPKK-NH2 (SEQ ID NO: 16) | ≥6000 |
| Tat-DAXXp | GRKKRRQRRRPPQ-KKSRKEKKQTGSGPLG-NH2 (SEQ ID NO: 58) | 13 ± 9 |
| Tat-scrDAXXp | GRKKRRQRRRPPQ-KKGRKQSGESLGTPKK-NH2 (SEQ ID NO: 66) | n.m. |
| Tat-DAXXp13 | GRKKRRQRRRPPQ-RKEKKQTGSGPLG-NH2 (SEQ ID NO: 14) | n.m. |
| Pip2b-DAXXp | (RXR)3-IHILFQNrRMKWHK-KKSRKEKKQTGSGPLG-NH2 (SEQ ID NO: 69) | 0.7 ± 0.2 |

All experiments are performed on a Biacore instrument. For each condition, the mean value of three independent experiments and the corresponding standard deviation are plotted.

Thereafter, the capacity of these peptides to inhibit apoptosis induced by staurosporine was evaluated. Apoptosis was determined using the Cell Death detection ELISA$^{PLUS}$ kit (Roche) measuring the DNA fragmentation.

In most publications, anti-apoptotic peptides currently available in the art are administrated 3-4 hours prior to apoptosis induction, which is poorly relevant to a clinical application. For that reason, the protocol used in the present study included administration of the peptides together with the staurosporine. FIG. 5B clearly shows a reduction of DNA fragmentation in primary cardiomyocytes of 44% using Tat-DAXXp and of 55% using Pip2b-DAXXp, respectively. This was not observed with CPP alone or with the Tat-scrDAXXp or Tat-ncDAXXp negative controls. The enrichment factor was calculated as suggested by the suppliers (DNA fragmentation of treated cells/DNA fragmentation of un-treated cells). To better compare the results, the DNA fragmentation (described by the enrichment factor) is related to the staurosporine-treated cells (=100%).

The anti-apoptotic effects of the peptides were also analyzed in murine NG118-15 (model for neuronal cells) (FIG. 5D), in murine C2C12 (model for muscle cells) (FIG. 5A) and in rat H9c2 (model for cardiac cells) (FIG. 5C). The highest reduction in DNA fragmentation were observed using Bpep-DAXXp in NG118-15 (66% reduction) using Tat-DAXXp in C2C12 (24% reduction) and Pip2b-DAXXp in H9c2 (31% reduction). This clearly reveals the importance of the optimal CPP choice for the appropriate application or biological context.

Furthermore, the binding epitope of FADD protein (SEQ ID NO: 8) was determined as described above for the DAXX epitope (details see above). As shown in FIG. 8A, Spot no. 11, corresponding to the peptide FADDp15 (VG-KRKLERVQSGLDL; SEQ ID NO: 9), has the higher signal intensity and the spots no. 10 and 12 (SEQ ID NO: 10 and SEQ ID NO: 11) share a minimal epitope sequence with FADDp15.

TABLE 4

Sequences derivate from FADD protein conjugated to Tat CPP.

| Tat-FADDp | GRKKRRQRRRPPQ-KRKLERVQS-NH2 (=SEQ ID NO: 59) |
| Tat-FADDp15 | GRKKRRQRRRPPQ-VGKRKLERVQSGLDL-NH2 (=SEQ ID NO: 60) |

Using a peptide library dissecting the length, the minimal fragment of FADDp15, which corresponds to FADDp (SEQ ID NO: 12; KRKLERVQS), was determined (see FIG. 8B). In cardiomyocytes, the decrease in apoptosis was 35% using the conjugates of Tat-FADDp and 57% using Tat-FADDp-15 (FIG. 9).

In Vivo Evaluation

Figure 11:
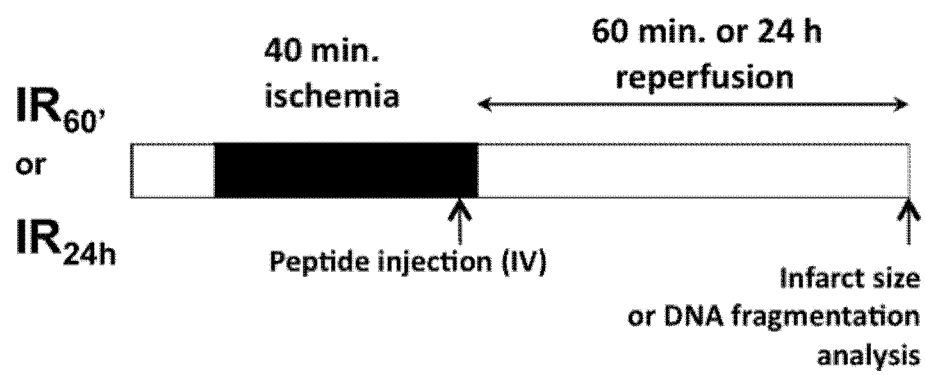
FIG. 11: In vivo experimental protocol. C57Bl6 mice underwent a surgical protocol of myocardial ischemia-reperfusion (IR). The black box represents the period of ischemia to which the mice were submitted. Infarct size or cell death measurements were performed at the end of surgery for each protocol (indicated by ↑). IR$_{60'}$: 40 minutes of Ischemia, 60 minutes of Reperfusion. IR$_{24h}$: 40 minutes Ischemia and 24 hours Reperfusion.

In a second step, the cardioprotective effects of DAXXp were evaluated in an in vivo model of myocardial ischemia-reperfusion. Acute myocardial ischemia and reperfusion were performed in C57Bl6 mice subjected to a surgical model of reversible coronary occlusion. Male mice (22-28 g) were anesthetized and ventilated via a tracheal intubation using a Harvard rodent respirator. Body temperature was maintained between 36.8° C. and 37.0° C. via a thermo-regulated surgical table. The chest was opened by left lateral thoracotomy and a reversible coronary artery snare occluder was placed around the left coronary artery. Mice were randomly allocated to two different surgical protocols of myocardial ischemia-reperfusion (FIG. 11). At the end of reperfusion, the artery was re-occluded and phtalocyanine blue dye was injected into the left ventricle cavity and allowed to perfuse the non-ischemic portions of the myocardium. To determine the effect of DAXXp on myocardial infarct size, peptides were administered intravenously (caudal vein) 5 minutes before reperfusion during the surgical protocol of ischemia-reperfusion. The control groups were treated with Tat or Pip2b peptide (for CPP alone). The dose of 1 mg/kg was chosen (μmolar range) and dose responses for 0.1 and 10 mg/kg were also tested.

At the end of reperfusion, mice were re-anaesthetized, the coronary ligature definitively tightened, the blue dye injected and the harvested left ventricles were dedicated to infarct size (TTC method, Schwartz et al, J Thromb. Thromb., 2000; 10: 181-187) or DNA fragmentation measurements (Cell death detection ELISA$^{PLUS}$ kit, Roche Diagnostics) in order to investigate the cardioprotective effects against ischemia-reperfusion injuries. The results obtained are shown in FIGS. 12 to 15.

When Tat-DAXXp (1 mg/kg) was injected intravenously in vivo, infarct size measured after 1 hour-reperfusion was decreased by 53.4% versus Tat peptide alone (p<0.01) (area at risk was comparable among groups; p=ns—FIG. 12A). This cardioprotection was correlated to a drastic decrease in specific DNA fragmentation, a hallmark of apoptosis, in left ventricles from Tat-DAXXp injected mice versus Tat-injected mice (see FIG. 12B). This cardioprotection was not observed with Pip2b-DAXXp or CPP alone or with the negative controls Tat-scrDAXXp (data not shown).

Figure 13:
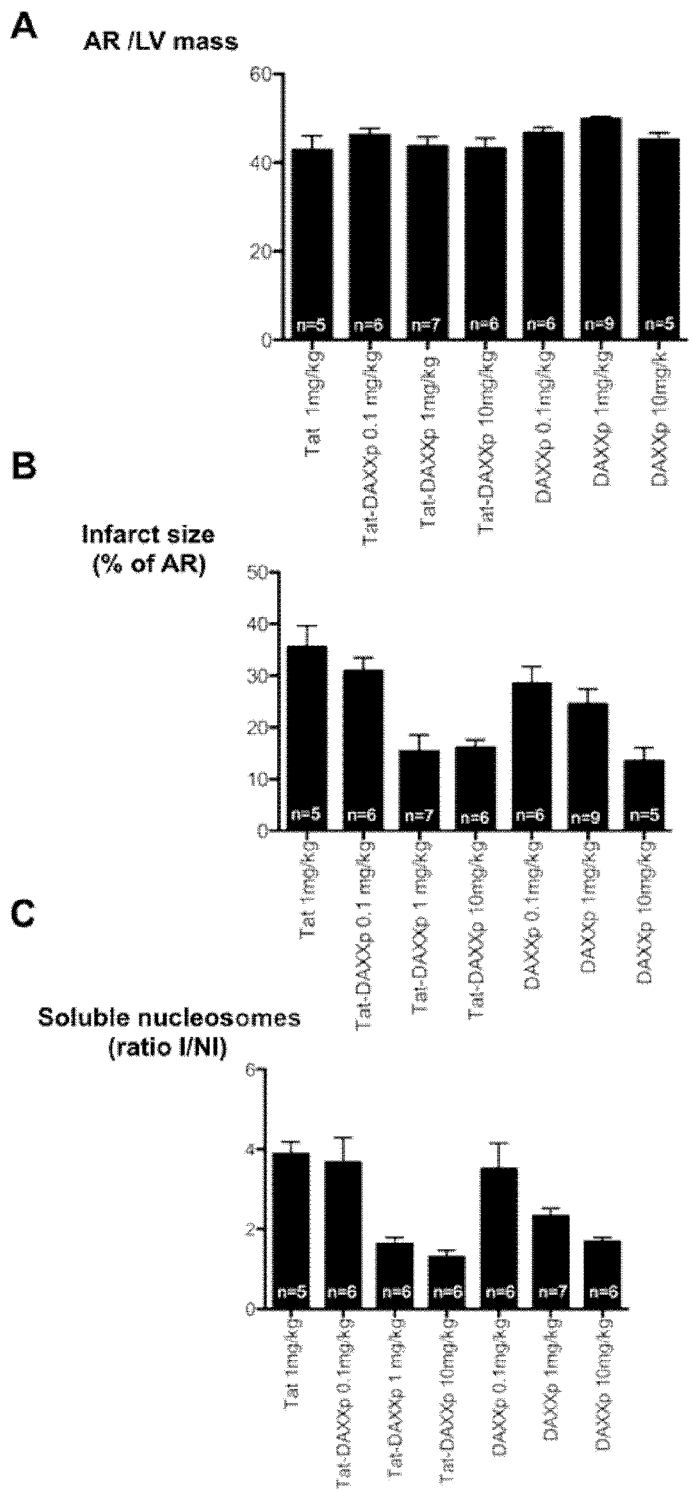
FIG. 13: Dose response for Tat-DAXXp and DAXXp in mice subjected to IR$_{60'}$. Infarct size (in % of area at risk) and internucleosomal DNA fragmentation determined by ELISA were quantified in mice subjected to IR$_{60'}$ and treated with Tat (1 mg/kg), Tat-DAXXp (0.1, 1 and 10 mg/kg) or DAXXp (0.1, 1 and 10 mg/kg) injected intravenously 5 minutes before reperfusion. Means±SEM were plotted for (A): Area at risk/LV mass (left ventricle), (B): Infarct size (in % of area at risk) and (C): (I/NI ratio) corresponding to the ratio of soluble nucleosome in the ischemic versus the non-ischemic portion of LV tissues.

FIG. 13 shows the dose response for Tat-DAXXp when injected at 0.1, 1 and 10 mg/kg and indicates that the maximal effect was obtained for a dose of 1 mg/kg. DAXXp (10 mg/kg) injected alone (without CPP) was able to protect the myocardium by decreasing both infarct size and DNA fragmentation to the same extent than Tat-DAXXp.

Figure 14:
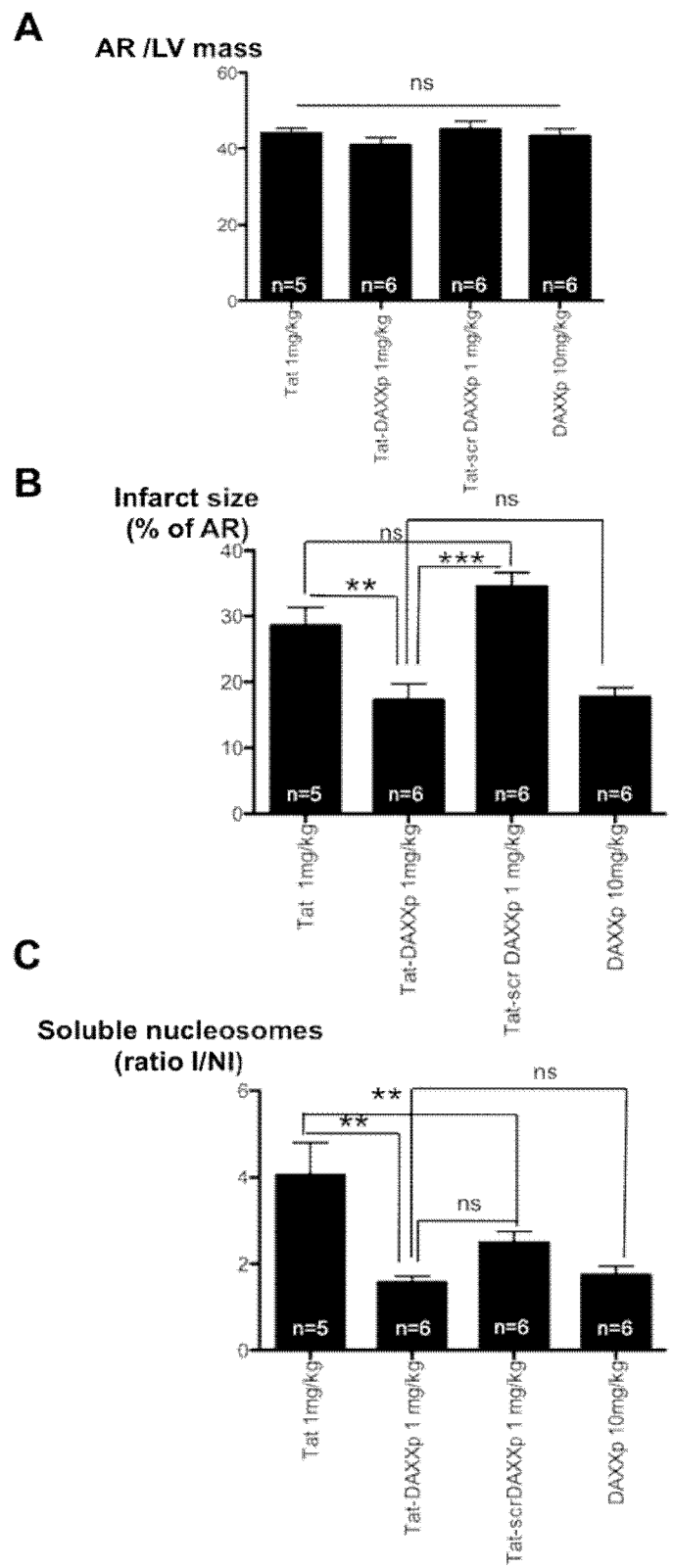
FIG. 14: Cardioprotective effects of Tat-DAXXp (1 mg/kg-IV) in mice subjected to IR$_{24h}$. Infarct size (in % of area at risk) and internucleosomal DNA fragmentation determined by ELISA were quantified in mice subjected to IR$_{24H}$ and treated with Tat, Tat-DAXXp or Tat-scrDAXXp (1 mg/kg) as well as with DAXXp (10 mg/kg) (IV injection 5 minutes before reperfusion). Means±SEM were plotted for (A): Area at risk/LV mass (left ventricle), (B): Infarct size (in % of area at risk) and (C): (I/NI ratio) corresponding to the ratio of soluble nucleosome in the ischemic portion versus the non-ischemic portion of LV tissues. Statistical analysis was done using One-way ANOVA with Neuman-Keuls post test for multiple comparisons (GraphPad Prism software). P<0.05, P<0.01 and P<0.001 versus Tat-DAXXp were noted *, , * respectively. P=ns (not significant) for P>0.05.

The cardioprotective effects of Tat-DAXXp were maintained when the reperfusion duration was prolonged from 1 hour to 24 hours (see FIGS. 14 and 15).

Figure 16:
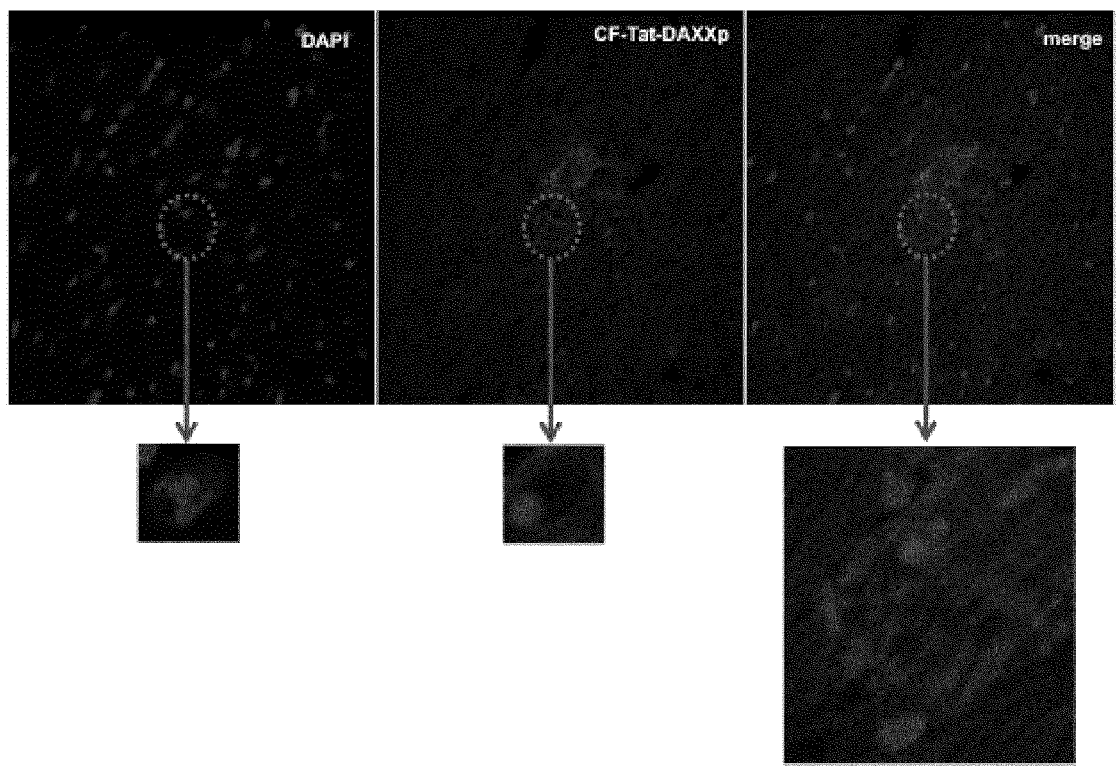
FIG. 16: Visualization of Tat-DAXXp constructs in the myocardium. Mice were injected at the time of reperfusion with 1 mg/kg CF-Tat-DAXXp construct (CF: Carboxyfluorescein). LV sections (20 μm) were obtained with a vibratome after 2 hours-paraformaldehyde fixation (4% PFA in phosphate buffer). 2 μm confocal images clearly showed a green labelling in myocytes indicating the presence of the peptidic construct in the cytosol. The circles highlight the presence of the peptidic construct in the DAPI-positive nucleus as observed in a few cases (oil-immersion X40).
Figure 17:
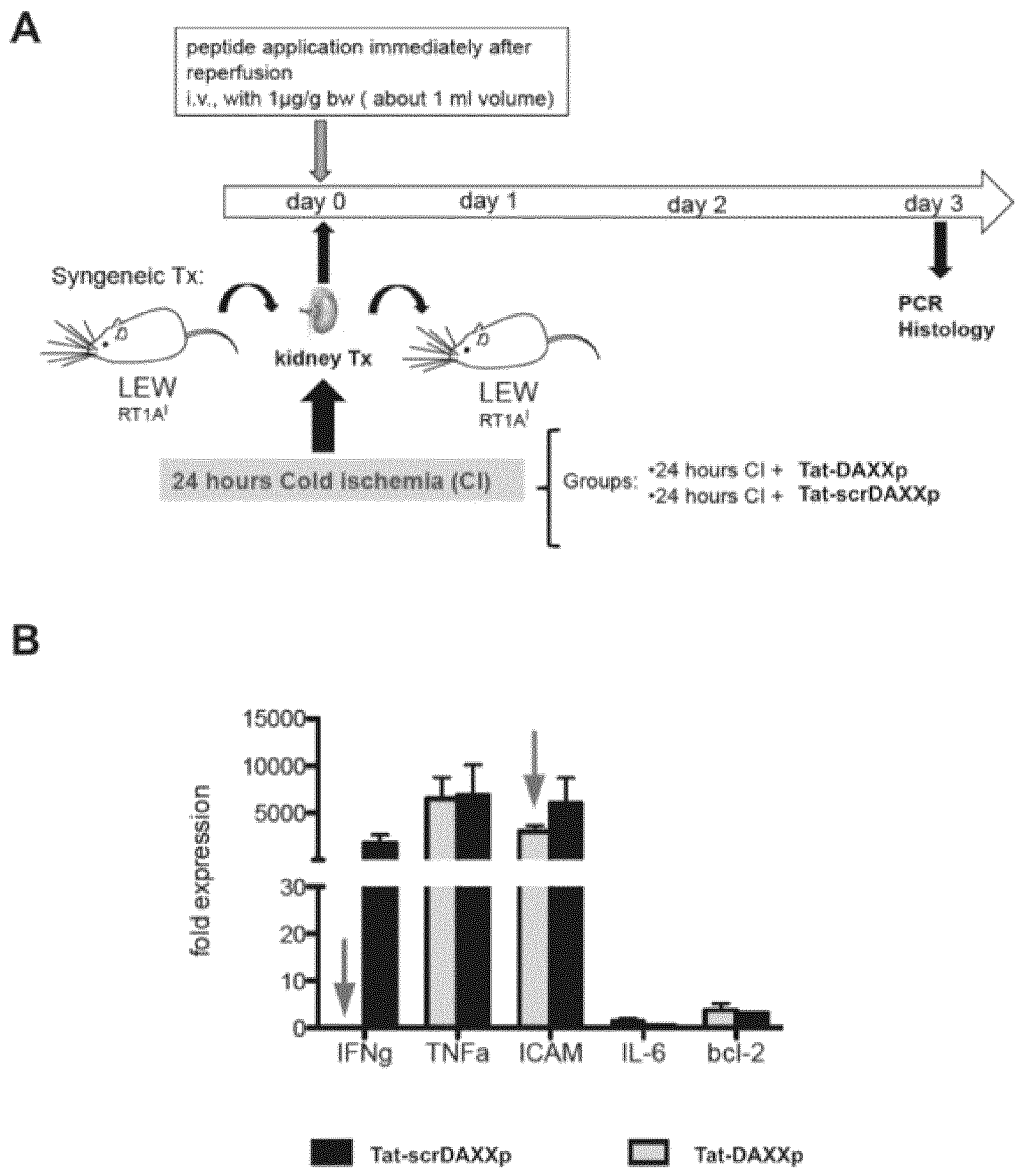
FIG. 17: Preliminary data on cold ischemia/reperfusion injury during kidney transplantation. Brain death and prolonged cold ischemia are major contributors to the poorer long-term outcome of transplants from deceased donor kidney transplants, with an even higher impact if expanded criteria donors ('marginal organs') are used. Targeting ischemia-reperfusion (IR) injury-related intragraft inflammation is an attractive concept to improve the outcome of those grafts. (A) Workflow of cold ischemia/reperfusion during kidney transplantation in rat. After a 24 h cold ischemia, the kidney graft was transplanted orthotopically into male LEW recipients using standard microsurgical techniques. Peptides were injected immediately after reperfusion in a single i.v injection at 1 mg/kg. Three days after transplantation, grafts were harvested for RT-PCR analysis (n=3). (B) Total RNA was reverse transcribed into cDNA and subjected to quantitative real-time RT-PCR utilizing the GENEAMP® 5700 Sequence Detection System (Applied Biosystems, Weiterstadt, Germany). The TAQMAN®-PCR reactions for ICAM-1, IFN-γ, TNF-α, interleukin (IL)-6 and bcl-2 (synthesized by Metabion, Martinsried, Germany) were performed in a final volume of 25 μl. These preliminary data show that in the presence of Tat-DAXXp, a reduction in mRNA expression of IFN-γ and ICAM-1 occurred in kidney graft 3 days after transplantation.

Confocal imaging revealed that CF-Tat-DAXXp (1 mg/kg) was localized both in the cytosol and in the nucleus of cardiomycytes in the left ventricle (FIG. 16).

Preliminary results obtained in an in vivo evaluation carried out in a renal transplantation model (Rat) showed that Tat-DAXXp (1 mg/kg) was able to protect from ischemia-reperfusion injuries in other clinical applications.

Throughout the present application, various references describe the state of the art to which the invention pertains. The disclosures of these references are hereby incorporated by reference into the present disclosure.

What is claimed is:

1. A peptide consisting of:
   a fragment of 16, 17, 18, 19, 20, 21, 22, 23 or 24 consecutive amino acid residues of the Death-Domain Associated (DAXX) protein of SEQ ID NO:1, wherein said fragment comprises the amino acid sequence set forth in SEQ ID NO: 5, or
   a fragment of 9, 10, 11, 12, 13, 14, 15, 16 or 17 consecutive amino acid residues of the Fas-Associated Death Domain (FADD) protein of SEQ ID NO: 8, wherein said fragment comprises the amino acid sequence set forth in SEQ ID NO: 12,
   wherein said peptide is capable of inhibiting cell apoptosis.

2. The peptide according to claim 1, wherein said peptide is a DAXX protein fragment and consists of the amino acid sequence set forth in SEQ ID NO: 5 or in any one of SEQ ID NOs: 17-44.

3. The peptide according to claim 1, wherein said peptide is a FADD protein fragment and consists of the amino acid sequence set forth in SEQ ID NO: 12 or SEQ ID NO: 9 or in any one of SEQ ID NOs: 45-57.

4. A conjugate comprising a peptide according to claim 1, wherein said peptide is linked to a Cell Penetrating Peptide.

5. The conjugate according to claim 4, wherein said peptide is linked to the Cell Penetrating Peptide through a linker.

6. The conjugate according to claim 4, wherein said Cell Penetrating Peptide is selected from the group consisting of Tat having the sequence set forth in SEQ ID No: 62, RXR having the sequence set forth in SEQ ID NO: 63, Bpep having the sequence set forth in SEQ ID NO: 64 and Pip2b having the sequence set forth in SEQ ID NO:65.

7. The conjugate according to claim 4, wherein said conjugate consists of the amino acid sequence set forth in SEQ ID NO: 58, SEQ ID NO: 59, or SEQ ID NO:60.

8. A pharmaceutical composition comprising an effective amount of at least one peptide according to claim 1, or a conjugate thereof, and at least one pharmaceutically acceptable carrier or excipient.

9. The pharmaceutical composition according to claim 8, wherein said peptide is a DAXX protein fragment and consists of the amino acid sequence set forth in SEQ ID NO: 5 or in any one of SEQ ID NOs: 17-44.

10. The pharmaceutical composition according to claim 8, wherein said peptide is a FADD protein fragment and consists of the amino acid sequence set forth in SEQ ID NO: 12 or SEQ ID NO:9 or in any one of SEQ ID NOs: 45-57.

11. The pharmaceutical composition according to claim 8, wherein the peptide is linked to a Cell Penetrating Peptide.

12. The pharmaceutical composition according to claim 11, wherein the peptide is linked to the Cell Penetrating Peptide through a linker.

13. The pharmaceutical composition according to claim 11, wherein the Cell Penetrating Peptide is selected from the group consisting of Tat having the sequence set forth in SEQ ID No: 62, RXR having the sequence set forth in SEQ ID NO: 63, Bpep having the sequence set forth in SEQ ID NO: 64 and Pip2b having the sequence set forth in SEQ ID NO: 65.

14. The pharmaceutical composition according to claim 8, wherein the conjugate consists of the amino acid sequence set forth in SEQ ID NO: 58, SEQ ID NO: 59, or SEQ ID NO: 60.

15. The pharmaceutical composition of claim 8 further comprising at least one additional biologically active agent.

16. The pharmaceutical composition according to claim 15, wherein said at least one additional biologically active agent is selected from the group consisting of cyclosporine A, Bcl-2 homology domain 4 (BH4), and combinations thereof.

17. A method for treating a disease or condition associated with apoptosis in a subject, comprising a step of:
   administering to said subject an effective amount of at least one peptide according to claim 1, or a conjugate thereof or a pharmaceutical composition thereof, wherein the conjugate comprises said peptide linked to a Cell Penetrating Peptide, wherein said disease or condition associated with apoptosis is selected from the group consisting of acute myocardial infarction (AMI), myocardial reperfusion injury, and myocardial ischemia.

18. The method according to claim 17 further comprising a step of: administering to said subject at least one additional biologically active agent selected from the group consisting of cyclosporine A, BH4, and combinations thereof.

19. The method according to claim 17, wherein, within the conjugate, the peptide is linked to the Cell Penetrating Peptide through a linker.

20. The method according to claim 17, wherein said Cell Penetrating Peptide is selected from the group consisting of Tat having the sequence set forth in SEQ ID No: 62, RXR having the sequence set forth in SEQ ID NO: 63, Bpep having the sequence set forth in SEQ ID NO: 64 and Pip2b having the sequence set forth in SEQ ID NO:65.

21. The method according to claim 17, wherein said conjugate consists of the amino acid sequence set forth in SEQ ID NO: 58, SEQ ID NO: 59, or SEQ ID NO:60.

* * * * *